United States Patent
Kumar et al.

(10) Patent No.: US 10,322,395 B2
(45) Date of Patent: Jun. 18, 2019

(54) PROCESS AND SYSTEM FOR PRODUCING PULP, ENERGY, AND BIODERIVATIVES FROM PLANT-BASED AND RECYCLED MATERIALS

(71) Applicant: Tyton Biosciences, LLC, Danville, VA (US)

(72) Inventors: Sandeep Kumar, Virginia Beach, VA (US); Peter Majeranowski, Danville, VA (US); Igor Kostenyuk, Winter Haven, FL (US); Iulian Bobe, Danville, VA (US); Florin Barla, Danville, VA (US)

(73) Assignee: Tyton Biosciences, LLC, Danville, VA (US)

( * ) Notice: Subject to any disclaimer, the term of this patent is extended or adjusted under 35 U.S.C. 154(b) by 0 days.

(21) Appl. No.: 15/822,414

(22) Filed: Nov. 27, 2017

(65) Prior Publication Data

US 2018/0071706 A1 Mar. 15, 2018

Related U.S. Application Data

(63) Continuation of application No. PCT/US2016/037188, filed on Jun. 13, 2016.
(Continued)

(51) Int. Cl.
*B01J 19/00* (2006.01)
*C10G 7/06* (2006.01)
(Continued)

(52) U.S. Cl.
CPC ....... *B01J 19/0053* (2013.01); *B01D 11/0207* (2013.01); *C10G 1/04* (2013.01);
(Continued)

(58) Field of Classification Search
CPC ..... B01D 11/00; B01D 11/02; B01D 11/0207; B01J 19/00; B01J 19/0053;
(Continued)

(56) References Cited

U.S. PATENT DOCUMENTS 8,546,560 B2 10/2013 Kilambi
8,637,718 B2 * 1/2014 Gupta .................. C10G 1/02
202/117

(Continued)

OTHER PUBLICATIONS

Toor et al., Hydrothermal liquefaction of biomass: A review of subcritical water technologies, 2011, Energy, 36, 2328-2342.*
(Continued)

*Primary Examiner* — Natasha E Young
(74) *Attorney, Agent, or Firm* — NK Patent Law

(57) ABSTRACT

The presently disclosed subject matter relates to an industrial system for processing various plant materials to produce marketable materials. Particularly, the system integrates subcritical water extraction technology and includes a pre-processing module and a two-stage extractor (processing module) with constant control of temperature, pressure, and/or residence time. In some embodiments, the final product of the disclosed system can include feedstock constituents for biofuel production (sugars and/or oil), biochar, raw materials for various industries (such as pulp for manufacturing paper or cellulose for use in various industries). The disclosed system can be modular or non-modular, stationary or mobile, and can include prefabricated elements with programmed automatic or manual operation so that it can be easily moved and/or assembled on site.

17 Claims, 6 Drawing Sheets

Related U.S. Application Data

(60) Provisional application No. 62/332,883, filed on May 6, 2016, provisional application No. 62/174,478, filed on Jun. 11, 2015.

(51) Int. Cl.

| | | |
|---|---|---|
| *C12P 7/10* | (2006.01) | |
| *C12P 7/64* | (2006.01) | |
| *C12M 1/00* | (2006.01) | |
| *D21D 1/14* | (2006.01) | |
| *D21H 11/02* | (2006.01) | |
| *D21C 1/02* | (2006.01) | |
| *D21C 3/02* | (2006.01) | |
| *D21C 3/22* | (2006.01) | |
| *D21C 5/02* | (2006.01) | |
| *D21C 7/00* | (2006.01) | |
| *D21C 11/00* | (2006.01) | |
| *B01D 11/02* | (2006.01) | |
| *C10G 1/04* | (2006.01) | |
| *D21B 1/14* | (2006.01) | |
| *C10G 1/06* | (2006.01) | |

(52) U.S. Cl.
CPC ............. *C10G 1/065* (2013.01); *C12M 21/12* (2013.01); *C12M 43/02* (2013.01); *C12P 7/10* (2013.01); *C12P 7/649* (2013.01); *D21B 1/14* (2013.01); *D21C 1/02* (2013.01); *D21C 3/02* (2013.01); *D21C 3/22* (2013.01); *D21C 5/02* (2013.01); *D21C 7/00* (2013.01); *D21C 11/0007* (2013.01); *D21H 11/02* (2013.01); *B01J 2219/00051* (2013.01); *B01J 2219/00162* (2013.01); *B01J 2219/00353* (2013.01); *B01J 2219/00891* (2013.01); *C10G 2300/1014* (2013.01); *Y02E 50/16* (2013.01); *Y02P 30/20* (2015.11); *Y02W 30/648* (2015.05)

(58) Field of Classification Search
CPC .... B01J 2219/00049; B01J 2219/00051; B01J 2219/00162; B01J 2219/00274; B01J 2219/00277; B01J 2219/00351; B01J 2219/00353; B01J 2219/00781; B01J 2219/00891; C10G 1/00; C10G 1/04; C10G 2300/00; C10G 2300/10; C10G 2300/1011; C10G 2300/1014; C12M 21/00; C12M 21/12; C12M 43/00; C12M 43/02; C12P 7/00–7/06; C12P 7/08; C12P 7/10; C12P 7/64; C12P 7/6436; C12P 7/649; D21B 1/00; D21B 1/04; D21B 1/12; D21B 1/14; D21C 1/00; D21C 1/02; D21C 3/00; D21C 3/02; D21C 3/22; D21C 5/02; D21C 7/00; D21C 11/00; D21C 11/0007; D21H 11/00; D21H 11/02; Y02W 30/50; Y02W 30/62; Y02W 30/648

See application file for complete search history.

(56) References Cited

U.S. PATENT DOCUMENTS

| | | | |
|---|---|---|---|
| 8,679,352 B2 * | 3/2014 | Olivier .................. | A23J 1/006 210/770 |
| 2013/0192123 A1 | 8/2013 | Maschmeyer et al. | |
| 2014/0234936 A1 * | 8/2014 | Kusuda .................... | C12P 7/10 435/165 |
| 2014/0275299 A1 | 9/2014 | Bedwell et al. | |
| 2014/0331993 A1 | 11/2014 | Kumar et al. | |
| 2014/0345341 A1 | 11/2014 | Fiato et al. | |

OTHER PUBLICATIONS

ISA/KR, International Search Report and Written Opinion of PCT Patent Application No. PCT/US2016/037188, dated Sep. 12, 2016.
WIPO, International Preliminary Report on Patentability of PCT Patent Application No. PCT/US2016/037188, dated Dec. 12, 2017.
EPO, Supplementary Partial European Search Report for European Patent Application No. 16808506, dated Dec. 3, 2018.
EPO, Extended European Search Report European Patent Application No. 16808506.6, dated Mar. 20, 2019.

* cited by examiner

The stage I and stage II are shown for simplifying the process description. In actual design, these stages can be integrated in single tublar reactor with multiple opening at different tube lengths and by maintaining a temperature gradient along the reactor.

PROCESS AND SYSTEM FOR PRODUCING PULP, ENERGY, AND BIODERIVATIVES FROM PLANT-BASED AND RECYCLED MATERIALS

CROSS REFERENCE TO RELATED APPLICATION

This application is a continuation of PCT Patent Application No. PCT/US2016/037188, now WO 2016/201414, filed on Jun. 13, 2016 and entitled "PROCESS AND SYSTEM FOR PRODUCING PULP, ENERGY, AND BIO-DERIVATIVES FROM PLANT-BASED AND RECYCLED MATERIALS", which claims priority to U.S. Provisional Patent Applications No. 62/332,883 filed on May 6, 2016 and entitled "MODULAR SYSTEM FOR INDUSTRIAL PROCESSING OF TOBACCO BIOMASS AND AGRICULTURAL WASTE AND BYPRODUCTS VIA SUBCRITICAL WATER ASSISTED HYDROLYSIS FOR PAPER AND PULP PRODUCTION AND RELATED METHOD", and No. 62/174,478 filed on Jun. 11, 2015 and entitled "MODULAR SYSTEM FOR INDUSTRIAL PROCESSING OF TOBACCO BIOMASS AND AGRICULTURAL WASTE AND BYPRODUCTS VIA SUBCRITICAL WATER ASSISTED HYDROLYSIS FOR SUGAR AND OIL EXTRACTION", the contents of which are all incorporated herein by reference in their entireties.

TECHNICAL FIELD

The presently disclosed subject matter relates to a modular or non-modular system for the industrial processing of plant material, wood, wood residue, algae, fungal biomass, agricultural waste, recycled materials, putrescible waste, and/or by-products or intermediate products thereof using subcritical water assisted hydrolysis to manufacture paper and pulp products, feedstock ingredients for the bioenergy industry, and other bio-derivative commodities.

BACKGROUND

Grasses, non-food crops, and agricultural waste have shown potential as a cost-effective "green" feedstock for biofuel and pulp/paper production and have become the subject of extensive research programs during the last decade. However, due to the limited amount of biomass that can be removed from the topography of a given land site, biomass must be transported from field to processor, adding costs to the manufacturing process. In addition, during the production of pulp and paper products, significant energy is required for heating, as well as relatively large quantities of chemical catalyst (typically sodium hydroxide in excess of 25% by volume), adding to the expense of manufacturing. It would therefore be beneficial to have an economically viable system and technology for processing plant biomass to produce feedstock ingredients for the bioenergy industry and/or green chemicals industry, as well as for the manufacture of pulp and paper products.

SUMMARY

In some embodiments, the presently disclosed subject matter is directed to a system comprising: a pre-processing portion having a mechanical processor/material handling for extraction of water soluble fermentable carbohydrates and an extractor portion having a reactor to which biomass and subcritical water is supplied to produce fermentable carbohydrates, oil, cellulose, pulp, and other bio-derivatives. In some embodiments, the reactor comprises a first operating condition at a first pressure and a first temperature that is maintained for a first defined period of time to break down carbohydrates of a first chain strength ("Stage 1") and a second operating condition at a second pressure and a second temperature that is maintained for a defined second period of time to break down remaining carbohydrates of a second chain strength ("Stage 2"). In some embodiments, the reactor comprises only one of the two operating conditions (Stage 1 or Stage 2). In some embodiments, the reactor comprises several operating conditions with Stage 1 and/or Stage 2 repeated.

In some embodiments, the presently disclosed subject matter is directed to a method for producing pulp for paper or as an additive to food products. Particularly, in some embodiments, the method comprises: processing a biomass into a processing size; treating the biomass with a catalyst comprising an alkaline catalyst (such as, but not limited to, NaOH and/or KOH) in an amount less than about 10 weight % to produce the pulp product; and using a subcritical water process to treat the biomass. Thus, the alkaline catalyst can be present in an amount of from about 0, 0.5, 1, 1.5, 2, 2.5, 3, 3.5, 4, 4.5, 5, 5.5, 6, 6.5, 7, 7.5, 8, 8.5, 9, 9.5, or 10 weight %.

In some embodiments, the presently disclosed subject matter is directed to pulp for paper made from tobacco biomass, wherein the pulp is made from a process comprising: processing a biomass into a processing size; using a subcritical water treatment process, treating the biomass with a catalyst comprising an alkaline catalyst in an amount less than about 10% to produce the paper pulp product. In some embodiments, the processing step comprises dry or fresh biomass and/or processing the biomass through a mechanical grinder, such as a hammer mill. In some embodiments, the subcritical water treatment process includes applying heat (at about 180° C. or less) to a reactor.

In some embodiments, the presently disclosed subject matter is directed to a method of producing biochar with favorable properties. The method comprises introducing biomass to the disclosed system comprising a pre-processing portion having a mechanical processor/material handling for extraction of water soluble fermentable carbohydrates and an extractor portion having a reactor to which biomass and subcritical water is supplied. The method further comprises adding oil to the system during the production of biochar, wherein the produced biochar exhibits more favorable properties (such as increased thermal value) compared to biochar produced from prior art methods.

In some embodiments, the presently disclosed subject matter is directed to a system comprising (a) a pre-processing portion having a mechanical processor/material handler for extraction of water soluble fermentable carbohydrates and preparation of material for further extraction; (b) an extractor portion comprising a reactor or a reactor assembly to which biomass and subcritical water is supplied, the reactor assembly having a first operating condition at a first pressure and a first temperature at a constant level that is held for a first defined period of time to break down carbohydrates of a first chain strength and a second operating condition at a second pressure and a second temperature at a constant level that is held for a defined second period of time to break down remaining oligo-carbohydrates of a second chain strength and fatty acids, wherein the system is repeatable until the recovery rate of the fermentable carbohydrates, fatty acid, or both reaches a desired yield. In some embodiments, the mechanical processor/material handler of the pre-processing portion includes a mechanical press for primary extraction of soluble carbohydrates, a wet or dry mill operably coupled to a material feeding mechanism, or both, and a storage tank for mixing with water or other liquid. In some embodiments, the system further comprises a variable speed and flow rate pump that pumps the mixed biomass and liquid downstream.

In some embodiments, the disclosed system further includes (a) a high pressure pump for increasing a pressure in the system, wherein a variable speed and flow rate are provided; (b) a pressure control valve for maintaining pressure in the first operating condition; (c) a pump for increasing the pressure of biomass in the flow channel to the second temperature and second pressure; and (d) a pressure control valve for maintaining pressure in the second pressure and second temperature section.

In some embodiments, the first operating condition comprises a pressure of about 0-300 psi and temperature of up to about 180° C. and the second operating condition comprises a pressure of about 301-3000 psi and a temperature of about 180° C. to 350° C.

In some embodiments, the pre-processing and first and second operating conditions are controlled and monitored by a centralized computer software able to maintain constant a desired pressure, temperature, and flow rate for a desired period of time; wherein the system comprises multiple sensors that are installed and connected to centralized computer managing software comprising a network in which technical information about major parameters such as pressure, temperature, flow, content level, is collected in real time, relayed to a managing system, and analyzed; wherein the above parameters are controlled and modified in real time.

In some embodiments, the reactor assembly comprises an assembly of one or more reactors followed by one or more pressure control valves, heat exchangers for cooling down the outputs from the reactor, and separators to collect valuable materials from the water phase and consequently recycle the water.

In some embodiments, the system is configured to produce as its final product feedstock constituents such as fermentable carbohydrates, fatty acids, and other compounds for biofuel production, biochar, pulp, cellulose, or raw materials for various industries, or combinations thereof from plant based materials or putrescible waste.

In some embodiments, the system is modular and scalable, stationary or mobile; wherein when in mobile form, the system can be mounted on one or more truck trailers, rail cars, shipping containers, other platforms used to transport from one site to another, or combinations thereof.

In some embodiments, the presently disclosed subject matter is directed to a method of producing pulp comprising: processing a biomass into a processing size; and using a subcritical water treatment process, treating the biomass with a catalyst that comprises an alkaline catalyst at a concentration of about 1.5 to 10 weight percent or less to produce a pulp product. In some embodiments, the pulp product has fiber length of about 0.000001-12 mm. In some embodiments, the method provides for continuous flow of material through the reactor such that the process provides for continuous manufacture of paper pulp product, cellulose, or combinations thereof.

In some embodiments, the disclosed method is modular and scalable, stationary or mobile; and wherein when in mobile form, the system can be mounted on one or more truck trailers, rail cars, shipping containers, other platforms used to transport from one site to another, or combinations thereof.

In some embodiments, the presently disclosed subject matter is directed to pulp, powdered cellulose, nano-cellulose, and dissolving cellulose produced from the method of claim 10, with fiber size of 0.000001-12 mm; wherein soluble carbohydrates and other soluble materials in water are produced as co-products. In some embodiments, the pulp is further exposed to a reactor at a temperature below 200° C.

In some embodiments, the presently disclosed subject matter is directed to a method of producing biochar from plant based or putrescible materials with increased properties, said method comprising: (a) introducing biomass into the disclosed system; (2) adding oil to the system during the production of biochar; wherein the produced biochar exhibits increased thermal value compared to biochar produced without the additional of oil to the system during production. In some embodiments, the biochar exhibits a thermal value in the range of about 20,000 to 30,000 BTU/pound, wherein about 14,000-16,700 BTU/pound is attributable to the added oil. In some embodiments, the method is modular and scalable, stationary or mobile; and wherein when in mobile form, the system can be mounted on one or more truck trailers, rail cars, shipping containers, other platforms used to transport from one site to another, or combinations thereof.

BRIEF DESCRIPTION OF THE DRAWINGS

The previous summary and the following detailed descriptions are to be read in view of the drawings, which illustrate particular exemplary embodiments and features as briefly described below. The summary and detailed descriptions, however, are not limited to only those embodiments and features explicitly illustrated.

DETAILED DESCRIPTION

Figure 1:
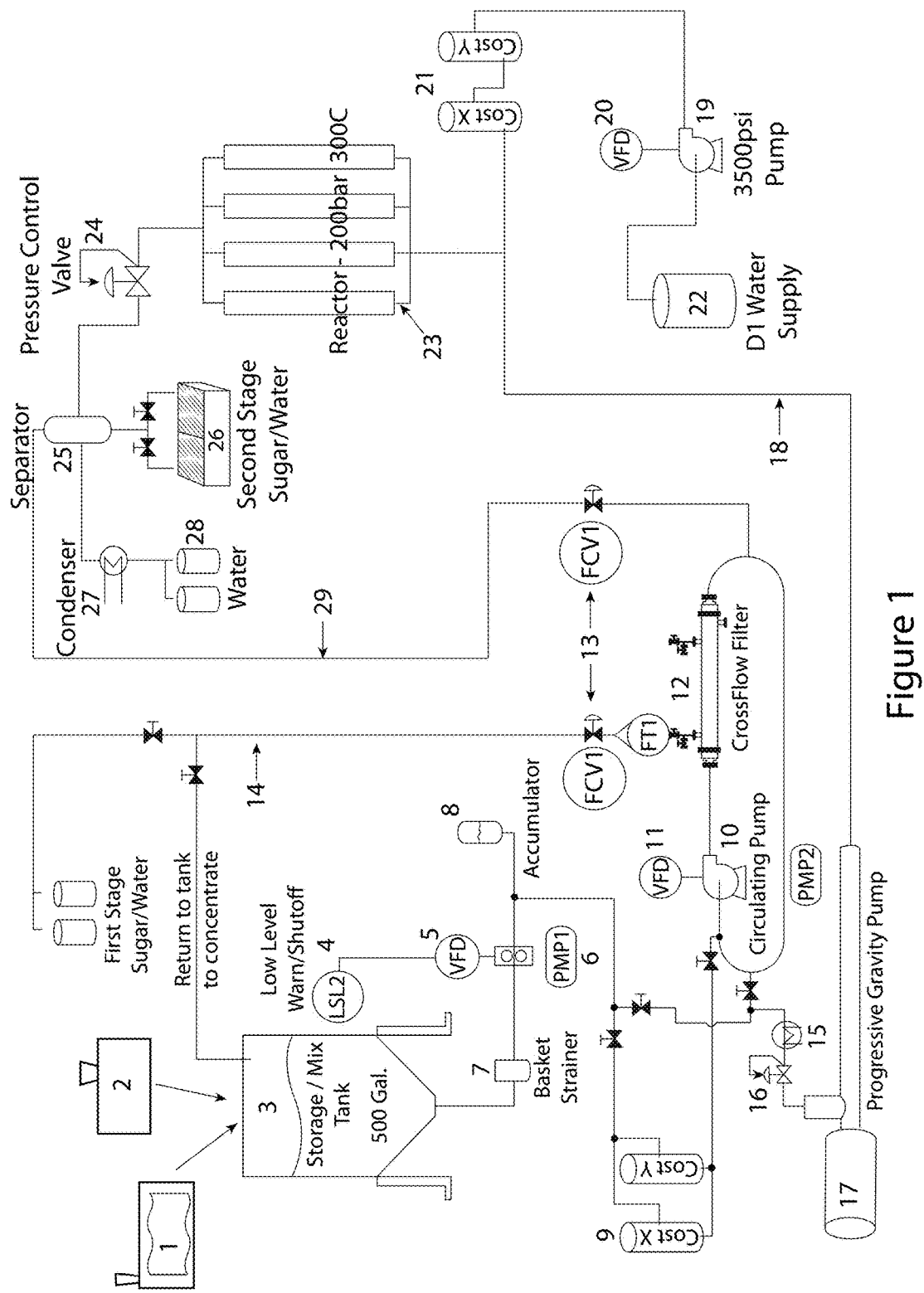
FIG. 1 is a diagram of a system for processing biomass according to some embodiments of the presently disclosed subject matter.

The presently disclosed subject matter will now be described more fully hereinafter with reference to the accompanying Examples, in which some (but not all) embodiments are shown. The presently disclosed subject matter can, however, be embodied in different forms and should not be construed as limited to the embodiments set forth herein. Rather, these embodiments are provided so that the instant disclosure will be thorough and complete, and will fully convey the scope of the embodiments to those of ordinary skill in the art.

Unless otherwise defined, all technical and scientific terms used herein have the same meaning as commonly understood by one of ordinary skill in the art to which the presently disclosed subject matter pertains. All publications, patent applications, patents, and other references mentioned herein are incorporated by reference in their entireties.

Following long standing patent law convention, the terms "a" and "an" mean "one or more" when used in the subject application, including the claims.

The term "about" as used herein, when referring to a value or to an amount of mass, weight, time, volume, diameter, or percentage is meant to encompass variations of +/−20%, 10%, 5%, 1%, or 0.1% from the specified amount, as such variations are appropriate to perform the disclosed method.

Although the term "step" may be expressly used or implied relating to features of processes or methods, no implication is made of any particular order or sequence among such expressed or implied steps unless an order or sequence is explicitly stated.

The presently disclosed subject matter relates to an industrial system for processing various plant materials to produce marketable materials. Particularly, the system integrates subcritical water extraction technology (also referred to as hydrothermal liquefaction technology ("HTL")) and includes a pre-processing module and a two-stage processing module. In some embodiments, the final product of the disclosed system can include feedstock constituents for biofuel production (sugars and/or oil), biochar, and raw materials for various industries (such as pulp for manufacturing paper products and/or cellulose for food or industrial products). The disclosed system can be modular or non-modular and can include prefabricated elements with programmed automatic or manual operation so that it can be easily moved and/or assembled on site. The disclosed system can be stationary or can be mobile and mounted on one or more truck trailers, railcars, shipping containers, or any other platform to be transported from one site to another.

In some embodiments, the disclosed system and methods can be used to produce biochar with improved properties. For example, in some embodiments, waste oil or virgin oil from biomass can be added during the biochar production process to produce biochar with improved properties. Particularly, in some embodiments, the oil can be added to biomass as an additional step during pretreatment and then further processed in a reactor assembly where the oil is absorbed into the biomass. Alternatively or in addition, biochar can be produced and then mixed with oil. Any oil (such as vegetable oil or any plant oil) or waste fat can be used. In some embodiments, about 0.8 to 1.5 liters of oil per kilogram dry biomass material can be used. Thus, at least about (or no more than about) 0.8, 0.85, 0.9, 0.95, 1.0, 1.05, 1.1, 1.15, 1.2, 1.25, 1.3, 1.35, 1.4, 1.45, or 1.5 liters oil/kg dry biomass can be used. In some embodiments, the produced biochar can exhibit an improved thermal value (BTU/pound) compared to biochar produced without the addition of oil. In some embodiments, biochar produced according to the disclosed method with tobacco biomass can exhibit a thermal value in the range of about 20,000 to 30,000 BTU/pound (about 14,000 to 16,700 BTU/pound can be attributed to the added oil).

Plant materials suitable for use in the disclosed system can comprise plant biomass, agricultural waste, putrescible domestic waste, and intermediate and byproducts thereof. The term "biomass" as used herein refers to any plant-derived matter (woody or non-woody) that is available. For example, biomass can include (but is not limited to) seeds, agricultural crop wastes and residues (such as corn stover, wheat straw, rice straw, sugar cane bagasse, hemp (*Cannabis sativa*), almond shells, peanut shells, tobacco stalks, and the like), grass crops (such as switch grass, alfalfa, winter rye, and the like), woody crops, wood wastes, and residues (such as trees, softwood or hardwood forest thinnings, barky wastes, branches, pine needles, sawdust, paper and pulp industry residues or waste streams, wood fiber, and the like), food waste, or any organic materials. It should be understood that biomass can include agricultural products, non-agricultural products, and all aerial and underground plant parts. Algal and fungal types of biomass can also be included under the term "biomass." In some embodiments, the biomass can be fresh, partially dried, completely dried, or mixtures thereof (i.e., high moisture, low moisture, and all levels in between). Specific example of biomass suitable for use in the disclosed system can include (but is not limited to) food crops, such as corn, wheat, soybean, cabbage, sugar beets, sugar cane, greens, and the like; non-food crops, such as tobacco, various grasses, bamboo, lavender, algae, Artemisia, hemp, and the like; lumber; chipped wood; agricultural waste (such as corn stover that can be used to produce powdered cellulose, for example); and plant-related industrial waste.

In addition, intermediate products made from plants can be used in the presently disclosed subject matter. For example, pulp and/or fiber can be produced from recycled paper and cardboard, cotton linters, various sacks (i.e., potato sacks, coffee sacks, and the like), barley and/or wheat after beer brewing, paper cups (including coated and uncoated paper cups).

As set forth in more detail herein below, the disclosed system integrates subcritical water extraction technology with variable computer controlled parameters to produce natural oils, sugars, pulp for paper manufacturing and food additive purposes, and other materials with market value from biomass. The term "subcritical water" as used herein refers to liquid water below the critical point. Advantageously, subcritical water is a non-toxic, environmentally benign, inexpensive, and green solvent that can be used as an alternative to conventional organic solvents traditionally used in the solvent extraction process (such as n-hexane). In the subcritical region, the ionization constant ($K_w$) of water increases with temperature and is about three orders of magnitude higher than that of ambient water, and the dielectric constant of water drops from 80 to 20. A low dielectric constant allows subcritical water to dissolve organic compounds, while a high $K_w$ allows subcritical water to provide an acidic medium for the hydrolysis of biomass components.

Because of its tunable solvent properties, subcritical water can be employed to extract many organic components from biomass.

In some embodiments, the disclosed system can be used to convert oil to hydrocarbons. Particularly, the extracted oils can be converted into biodiesel through transesterification process or into renewable diesel and advanced biofuels (jet fuel, green diesel) though the catalytic hydrodeoxygenation process, as examples.

In some embodiments, the disclosed system can be used to produce activated carbon with reaction conditions of about 500° C. Particularly, a catalyst such as a catalyst that includes zinc can be added to the process to bind with the biochar.

In some embodiments, the system comprises prefabricated modular elements with programmed automatic or manual operation, such that it can be easily moved in and assembled on site without undergoing expensive and time-consuming system elements stoppage. Thus, the disclosed system can include a combination of interchangeable and replaceable modules and sections that allow flexible operation, switching from one type of feedstock to another. In some embodiments, the disclosed system is transported to a biomass capture facility or site.

Combining the disclosed modular structure with subcritical water extraction allows an operator to run equipment in programmed mode in accordance with well-established protocols, but also provides a wide range of opportunities for experimentation and introduction of modifications of known technologies along with development of new technologies. The modular elements of the system can be referred to as "sections" herein.

The disclosed method includes a pre-processing module and a 2-stage processing module (extractor). For pulp and paper production from biomass, the presently disclosed subject method comprises processing a biomass into a processing size and using a subcritical water treatment process to treat the biomass with a catalyst to produce the paper pulp product. In some embodiments, the catalyst can comprise sodium hydroxide (NaOH) at a concentration of no more than about 8, 7.5, 7, 6.5, 6, 5.5, 5, 4.5, 4, 3.5, 3, 2.5, or 2 weight %. In some embodiments, the amount of NaOH can be about 2 to about 5 weight %.

The pre-processing module comprises a disintegrating device/material handling to enable extraction of water soluble compounds and water ("juice") from biomass, and to downsize the biomass for later treatment in the processing module. In some embodiments, the juice can comprise water soluble fermentable carbohydrates (such as, but not limited to, glucose, galactose, and/or mannose). As illustrated in FIG. 1, the disintegrating device can comprise a device that functions to break down the plant biomass using pressure. In some embodiments, the disintegrating device can be a specialty screw press that comprises a solid phase extraction mechanism, a counter pressure mechanism, an air compressor (1-100 psi), an air pressure control, a steam generator, a liquid phase separate, and/or a resulting cake collector. In some embodiments, the disintegrating device can include a grinding element (such as a hammer mill or industrial shredder) with a grinding mechanism suitable for low moisture biomass disintegration. The disintegrating device and/or grinding element function to grind and/or disintegrate bulk plant biomass for further processing, including (but not limited to) extracting juice with water soluble sugars from fresh biomass, downsizing biomass particles, and/or crushing low moisture materials for further processing in the processing module. In some embodiments, the disintegrating device can include a wet mill, wherein water and optionally other soluble compounds can be added to the biomass and steeped as part of the milling process, prior to grinding.

The processing module can also include several optional features, including (but not limited to) a material conveying pneumatic system comprising an air compressor; tubing and air filtration bags for milling dry plant material, agricultural byproducts, and/or cake resulting from juicing fresh biomass; computerized controls that can remotely control input, output, and/or intermediate parameters; computerized controls that comprise optional shutoff in case of an emergency situation; one or more reaction tubes (reactors) assembled as a structural group (i.e., several reactors connected to a pre-processed biomass feeding system in some embodiments).

The processing module comprises stage 1 processing (which can include low pressure/low temperature conditions) and stage 2 processing (which can include high pressure/high temperature conditions). In some embodiments, during stage 1 processing of the mixed biomass material, a low-temperature subcritical water extraction takes place within a reactor. Thus, the reactor has a first operating condition at a first pressure and temperature (0-300 psi and 200° C. or less) that is maintained for a defined period of time to break down carbohydrates of a first chain length. Thus, the first pressure can be at most (or at least) about 300, 290, 280, 270, 260, 250, 240, 230, 220, 210, 200, 190, 180, 170, 160, 150, 140, 130, 120, 110, 100, 90, 80, 70, 60, 50, 40, 30, 20, or 15 psi. The first temperature can be at most about 200, 195, 190, 185, 180, 175, 170, 165, 160, 155, 150, 145, 140, 135, 130, 125, 120, 115, 110, 105, 100, 95, 90, 85, 80, 75, 70, 65, 60, 55, 50, 45, 40, 35, 30, or 25° C. In some embodiments, the first pressure and/or temperature can remain constant for the defined time period.

In some embodiments, the time period can be about 5 to 20 minutes (i.e., about 5, 6, 7, 8, 9, 10, 11, 12, 13, 14, 15, 16, 17, 18, 19, or 20 minutes). Thus, during stage 1 processing, carbohydrates that exist in the biomass ("free sugars") are recovered. In addition, sugars released from starch at the lower temperature and pressure conditions are also recovered, such as amylose (500-20,000 D-glucose units) and amylopectin (up to 2,000,000 D-glucose units). After this process is complete, the sugars can be separated out from the biomass slurry using a separator in some embodiments. In some embodiments, a return pipeline can be attached to the separator and to the low pressure/low temperature section to recycle water, along with a flow control valve to balance the pressure and return water supply.

Stage 1 processing includes a mixing junction that houses and/or mixes biomass slurry and water. In some embodiments, the mixing junction comprises a tank that allows for storage and mixing of the biomass slurry and the water. Crushed biomass slurry is transported to the mixing junction by, for example, a high pressure pump. In some embodiments, water (such as deionized water) can also be transported to the mixing junction using, for example, a high pressure pump. It should be appreciated that mixing junction can be sized to house a desired amount of biomass for a particular application (i.e., 100-1000 gallons in some embodiments). In some embodiments, the mixing junction includes one or more heating elements to raise the temperature of the biomass slurry/water mixture to a desired level. In some embodiments, stage 1 processing also includes a return loop that comprises flow control valves, piping, or other flow channels attached to a crossflow filter for partially recycling incoming feed and enriching the biomass/water mixture in the mixing junction. In some embodiments, stage 1 processing can include a condenser for capturing steam, reducing the temperature of the steam, and returning water to the liquid phase.

In some embodiments, the mixing junction can include a low-level sensor and shut off (to enable system shutoff when a low volume is detected), basket strainer for capturing large pieces of biomass, an accumulator to balance the pressure in the system, at least two variable frequency devices, a water pump, a circulating pump, two flow control valves, outlets for sampling, and/or additional sensor installation. In some embodiments, the pumps, heaters, accumulator, and flow control valves maintain pressure at about 0-300 psi and temperature of 200° C. or less in the reactor assembly.

During stage 2 processing of the biomass material processed in stage 1, the reactor assembly processes the material under a second operating condition at a second pressure and temperature (301-3,000 psi and 180° C.-350° C.) that is held for a defined period of time to break down the remaining carbohydrates of a second chain length. Thus, the pressure can be no more than (or no less than) about 301, 350, 400, 450, 500, 550, 600, 650, 700, 750, 800, 850, 900, 950, 1000, 1050, 1100, 1150, 1200, 1250, 1300, 1350, 1400, 1450, 1500, 1550, 1600, 1650, 1700, 1750, 1800, 1850, 1900, 1950, 2000, 2050, 2100, 2150, 2200, 2250, 2300, 2350, 2400, 2450, 2500, 2550, 2600, 2650, 2700, 2750, 2800, 2850, 2900, 2950, or 3000 psi. The temperature can be no more than (or no less than) about 180, 185, 190, 195, 200, 205, 210, 215, 220, 225, 230, 235, 240, 245, 250, 255, 260, 265, 270, 275, 280, 285, 290, 295, or 300° C. In some embodiments, the second pressure and/or temperature can remain constant for the defined time period.

In some embodiments, the time period can be about 0.0833 minutes (5 seconds) to about 40 minutes, such as a time of at least (or no more than) 0.0833, 0.167, 0.25, 0.333, 0.4165, 0.5, 0.583, 0.67, 0.75, 0.833, 0.917, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 20.5, 21, 21.5, 22, 22.5, 23, 23.5, 24, 24.5, 25, 25.5, 26, 26.5, 27, 27.5, 28, 28.5, 29, 29.5, 30, 30.5, 31, 31.5, 32, 32.5, 33, 33.5, 34, 34.5, 35, 35.5, 36, 36.5, 37, 37.5, 38, 38.5, 39, 39.5, or 40 minutes. In some embodiments, the carbohydrates of the second chain length represent the leftover non-broken down starch from the Stage 1 processing, and/or the cellulose and/or hemicellulose (300-10,000 D-glucose units).

The material is then separated into a solid phase biochar and/or pulp production) and liquid phase (sugar, oil, other solubles, and water). In some embodiments, the disclosed system enables plant oils and fatty acids to be extracted from biological tissues without using harsh organic solvents. The high pressure and high temperature section can comprise one or more of the following: a progressive cavity pump, an additional high pressure pump equipped with a variable frequency device, ionized or deionized water supply and water heaters for proper pre-treated feed slurry flow and temperature and system pressure. In some embodiments, the chemical formula representing the breakdown of material during the stage 1 and stage 2 processing is illustrated as: $(C_6H_{10}O_5)_n + nH_2O \rightarrow nC_6H_{12}O_6$. In some embodiments the high temperature/high pressure section comprises a pressure control valve, separator to collect valuable materials in the water phase, and a condenser for cooling and collecting water from steam for recycling. In some embodiments, when solid phase pulp and/or cellulose products are produced, the pulp is bleached using standard bleaching agents (i.e., hydrogen peroxide, sodium hypochlorite) and equipment according to know methods.

Thus, the disclosed system performs one or more of the following functions: extraction of water-soluble compounds and moisture ("juice") from fresh biomass, preparation of the resulting cake and conveying it to the mixing junction (which can be a mixing tank), disintegrating low moisture biomaterials, adjusting moisture content in the mixing junction, processing by running the slurry through a low pressure/low temperature stage (stage 1), running processed matter through high pressure/high temperature stage (stage 2), enriching the resultant extract with products of interest by removing excess moisture, and collecting the materials of interest. In some embodiments, the disclosed system provides for continuous flow of material through the reactor such that the process provides for continuous manufacture of product. In some embodiments, the products can include fermentable carbohydrates, oils, and/or biochar. In some embodiments, the product can be a paper product, such as (but not limited to) kraft pulp (paper, cardboard, and the like), powdered cellulose (can be used as a food additive), dissolving cellulose (for use in production of rayon, dynamite, and the like), and nano-crystalline cellulose (or micro-crystalline cellulose), and fermentable carbohydrates. Further, in some embodiments, the disclosed system can be used to produce specialized paper products (i.e., paper products comprising additives), such as charged pulp used in diaper products and other applications in the medical field, or paper infused with silver, copper, or other metals.

In some embodiments, the pre-processing module and/or processing module can be assembled as a pre-fabricated housing structure. The structure can include erected weight-bearing frames (such as metal frames) that carry support surfaces for the various sections of the extractor, foundation and top frames attached to upright elements of the support frames. In some embodiments, one or more elements of the pre-processing or processing modules are monitored and controlled by centralized computer software to maintain a certain preset pressure and/or temperature constantly for a desired residence time. To this end, multiple sensors can be installed and connected to the centralized computer managing software network so that technical information about various parameters (temperature, pressure, flow, content level, and the like) can be collected in real time and relayed to a managing system where the information is analyzed to control/modify the parameters in real time.

It should be appreciated that in some embodiments, the disclosed methods use solely water as a solvent and medium for processing feedstock. In some embodiments, the disclosed methods can be used for sequentially converting water-insoluble naturally occurring materials such as cellulose, hemicellulose, and lignin into oligomers and monomer sugar molecules, such as sucrose, fructose, glucose, and the like.

FIG. 1 illustrates one embodiment of a system according to some embodiments of the presently disclosed subject matter. Specifically, the system comprises disintegrating device 1 (which in some embodiments can be a specialty screw press or any type of mechanical grinder or processor) and grinding element 2 (which can be hammer mill with a grinding mechanism for low moisture biomass disintegration). The grinding element can further include a blower for transferring ground biomass to the mixing junction and an air filtration system to contain dust resulting from grinding. In some embodiments, the grinding element can be connected to a material feeding system. After the disintegrating device and/or grinding element extracts juice from the biomass and downsizes the biomass particles, the resultant cake is conveyed to mixing junction 3, which in some embodiments can be a storage/mixing tank. In some embodiments, the cake is mixed with water in mixing junction 3 to adjust moisture content and/or to improve flow properties as desired. After mixing with water, the biomass can be referred to as a "slurry."

As illustrated in FIG. 1, the mixing junction can be associated with valve 4 that disconnects the extractor feed system when the volume of the mixing junction is below a threshold level. Pump 6 ensures proper biomass/water mix flow at the initial stage of processing. In some embodiments, the disclosed system comprises variable frequency device ("VFD") 5 that functions to control the frequency of pump 6 motor as it pumps the mixed biomass and liquid downstream. As shown, straining device 7 (such as a basket strainer or separation/filtering mechanism) captures larger pieces of ground biomass leaving holding device 3 and prevents the system from clogging. In some embodiments, the system can comprise accumulator 8 that compensates for pressure changes in the system and prevents potential mechanical damage from other system elements. As with the other elements disclosed herein, the accumulator can be an optional feature of the disclosed system.

In some embodiments, the disclosed system comprises at least one heating element 9 for raising the temperature and pressure of the slurry to a desired level. Heating element 9 can provide direct or indirect heating. As used herein, "direct heating" refers to the injection of steam or heated air/gas directly into the slurry to elevate the temperature. As used herein, the term "indirect heating" refers to a process wherein a device generating heat is used to transfer heat to the slurry, but without direct contact between the biomass and the heaters. In some embodiments, the disclosed system can comprise circulating pump 10 to further increase the pressure in the system as desired. In some embodiments, circulating pump 10 can be a water pump. In some embodiments, VFD 11 can be present to control the frequency of pump 10 motor.

In some embodiments, the disclosed system comprises pressure control valve 12 for maintaining pressure in low pressure/low temperature areas of the reactor within programmed parameters (i.e., a first operating condition of low pressure/temperature or a second operating condition of high pressure/temperature). In addition, in some embodiments, the disclosed system comprises flow control valve 13 for maintaining the flow rate in the pipes within programmed parameters.

In some embodiments, the disclosed system includes return loop 14 that functions to enrich the processed biomass with desired compounds of interest. For example, the biomass slurry can be enriched with catalysts, including, but not limited to, alkaline catalysts (such as NaOH) that bind to lignin and relax fibers in the biomass slurry. In addition, the pH of the biomass slurry can be adjusted to a desired level using loop 14. In some embodiments, the disclosed system comprises condenser 15 that functions to capture water from the steam/vapors and return it to the biomass slurry. In some embodiments, the disclosed system comprises pressure control valve 16 for maintaining pressure in low pressure/low temperature section within programmed parameters. In some embodiments, the disclosed system comprises progressive cavity pump 17 for raising the pressure in high pressure/high temperature section of the extractor and to feed the pre-processed biomass to reactor assembly 23. In some embodiments, the high pressure/high temperature section is the site of extraction of water soluble and insoluble natural constituents from broken cells and tissues of the biomass slurry. High pressure feed 18 allows the slurry to reach reactor assembly 23.

In some embodiments, the disclosed system comprises pump 19 (such as a high potency pump) to enrich the slurry with high pressure water (i.e., deionized water in some embodiments) for use in the reactor assembly. In some embodiments, the disclosed system comprises variable frequency modulator 20 to control the frequency of the motor of pump 19. In some embodiments, the system includes at least one additional heating element 21 to increase the temperature of the supplied water from water supply unit 22.

In some embodiments, reactor assembly 23 can include several flow channel reactors. For example, the reactor assembly can operate at about 200 bars and about 300° C. Reactor assembly 23 can include pressure control valve 24 for maintaining pressure in high pressure/high temperature section within programmed parameters. In some embodiments, reactor assembly 23 can include seven reactors of variable diameters (such as, but not limited to, about 0.5-10 cm each). In some embodiments, the reactors can be arranged vertically. In some embodiments, the reactors can be constructed from stainless steel. The reactor assembly is the site of chemical conversion of plant-originating biopolymers into smaller size molecules that can be further used for extraction of water soluble sugars. In addition, the reactor assembly enables the transformation of the physical properties of initial plant biomass to produce raw materials for further products with market value, such as paper. In some embodiments, the described above process can be carried out in subcritical water extraction reactors comprised in a high pressure/high temperature section of the extractor.

In some embodiments, the disclosed system comprises separator unit 25 for separating steam from liquid exiting the reactor. The system can comprise collector 26 for collecting products of interest in the liquid phase for further concentration, and condenser 27 for collecting and recycling water. In some embodiments, water collector 28 can be used for collecting water and re-routing it back to the system. In some embodiments, the system comprises return loop 29 for partially feeding low pressure/low temperature section with slurry.

Figure 2:
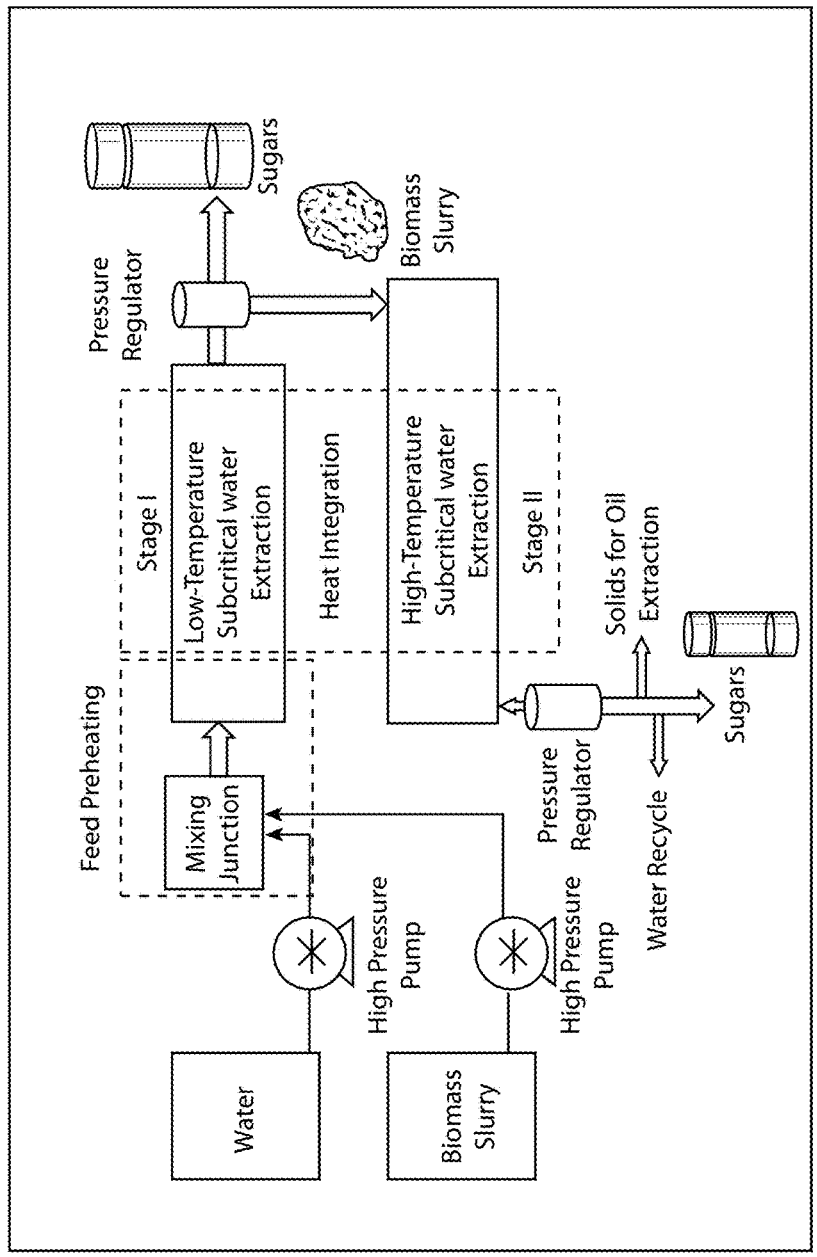
FIG. 2 is a diagram of a system for processing biomass according to some embodiments of the presently disclosed subject matter.

FIG. 2 illustrates one embodiment of the disclosed system. Specifically, the processing module is illustrated wherein biomass slurry is propelled with a pump (which in some embodiments can be a high pressure pump) to the mixing junction. Optionally, water (i.e., deionized water) is propelled with a pump (which can be a high pressure pump) towards the mixing junction, where it is mixed with the biomass slurry.

The biomass slurry proceeds to the processing module where a two-stage extraction takes place. In stage 1 processing of the slurry, a low-temperature, subcritical water extraction occurs within the reactor assembly. Thus, the reactor assembly has a first operating condition at a first pressure (0-300 psi in some embodiments) and a first temperature (200° C. or less in some embodiments) held for a first defined period of time to break down carbohydrates of a first chain length. After this process is complete, the pressure regulator and separator separate out sugars from biomass slurry. In stage 2 processing of the material processed in stage 1, the reactor assembly processes the material under a second operating condition at a second pressure (about 301 to 3,000 psi in some embodiments) and a second temperature (about 200° C. to 350° C. in some embodiments) and is held for a defined second period of time to break down remaining carbohydrates of a second chain strength. The material is then separated into solids for oil extraction, sugars, and water. In some embodiments, the reactor assembly can comprise subcritical water extraction.

Figure 3:
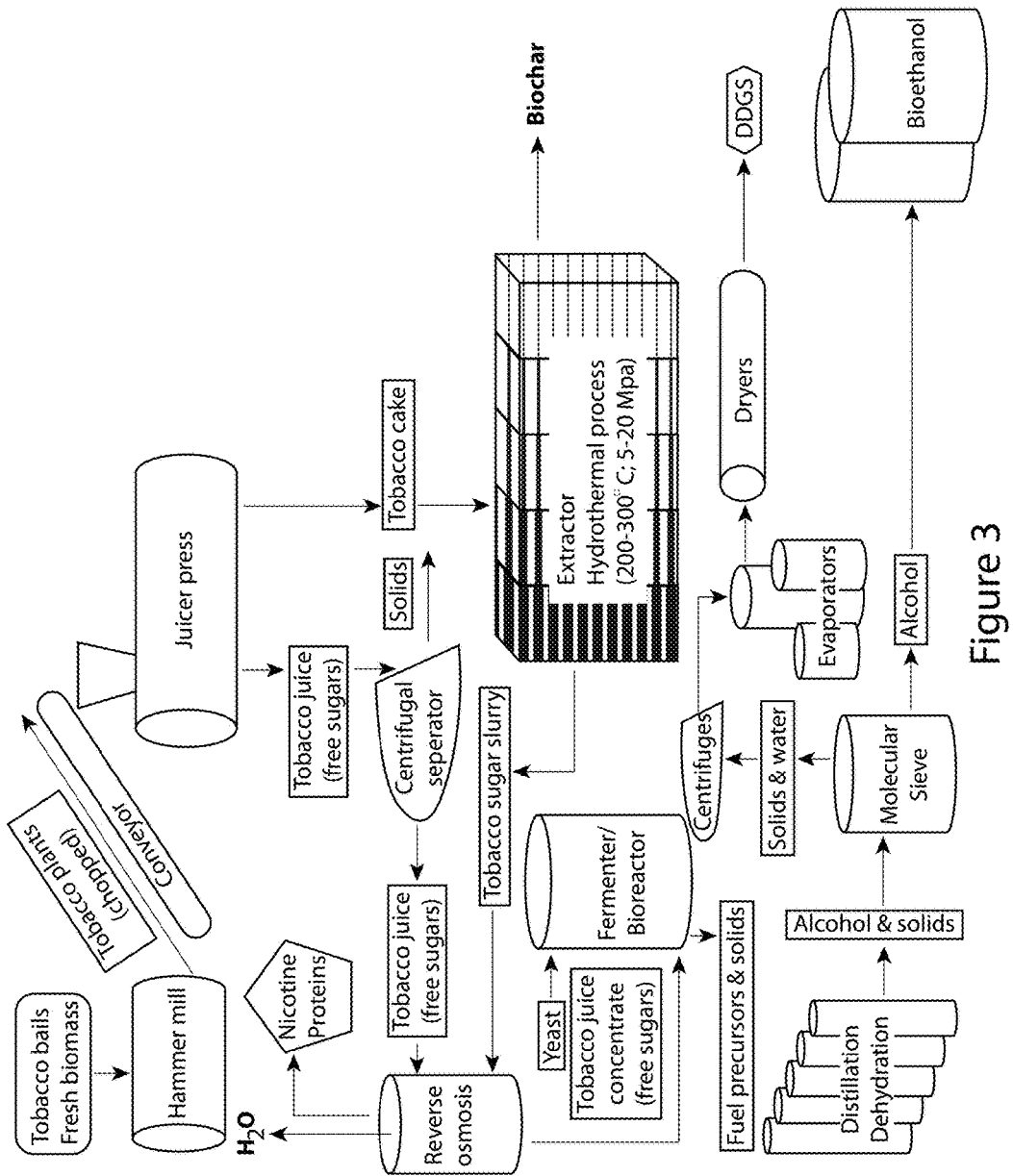
FIG. 3 is a diagram of a system for processing biomass according to some embodiments of the presently disclosed subject matter.

FIG. 3 illustrates one embodiment of the disclosed system. Particularly, biomass (which in some embodiments can be tobacco bales) are provided to a pre-processing module wherein a disintegrating device (such as a hammer mill/material handler) breaks the biomass into smaller pieces. The chopped biomass is then translated to a juicer press using, for example, a conveyor or other similar device. The juicer press separates tobacco cake and tobacco juice. The tobacco cake is fed into the reactor assembly. The tobacco juices are separated with a centrifuge and solids are intermixed with the cake for feeding into the reactor assembly, and liquids are processed through a membrane filtration process into nicotine proteins and water, where the water is returned to the main tank.

Biochar is a byproduct of the processing steps carried out in the reactor assembly, with the biochar being used for any other suitable process, or as a suitable feedstock or material for other uses such as fertilizer, and the like. Tobacco sugar slurry from the reactor assembly is processed in the membrane filtration module/chamber, with water and nicotine byproducts formed, as well as tobacco juice concentrate that is transported to a fermenter/bioreactor. In the fermenter/bioreactor, yeast and/or bacteria is added to produce fuel precursors and other solids. A distillation/dehydration process produces alcohol and solids, which are then transported to a molecular sieve. A molecular sieve segregates the solids and water, which are then passed through a centrifuge and then into at least one evaporator. At least one dryer can be utilized to produce distiller's dried protein cakes/protein concentrates. The molecular sieve also segregates alcohol, which is then formed into bioethanol.

Figure 4A:
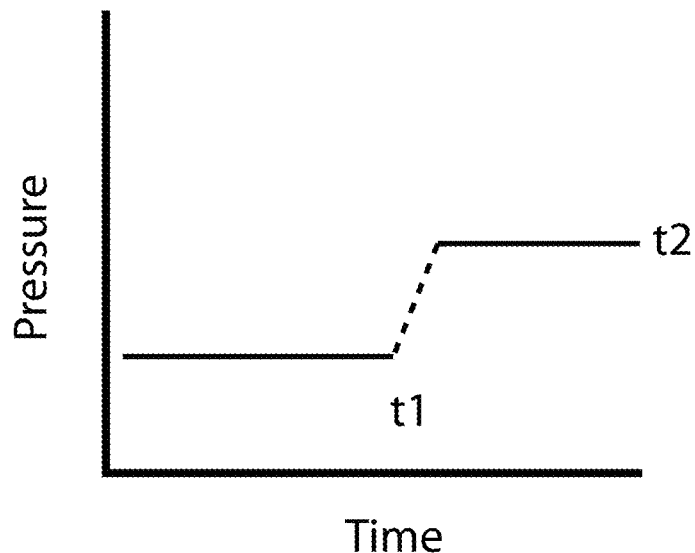
FIG. 4a is a graph of the increase in pressure versus time during the processing module in accordance with some embodiments of the presently disclosed subject matter.
Figure 4B:
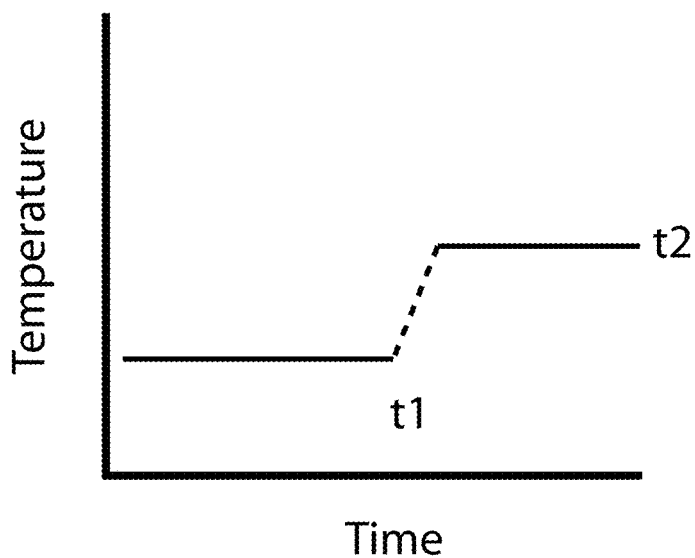
FIG. 4b is a graph of the increase in temperature versus time during the processing module in accordance with some embodiments of the presently disclosed subject matter.

FIGS. 4a and 4b are graphs that illustrate the pressure and temperature in the reactors over time. Specifically, FIG. 4a shows that up until time t1, a first pressure is used. From time t1 to time t2, a second (higher) pressure is used. Similarly, FIG. 4b shows that up until time t1, a first temperature is used, and from time t1 to time t2, a second (higher) temperature is used.

Particular embodiments and features have been described with reference to the drawings. It is to be understood that these descriptions are not limited to any single embodiment or any particular set of features, and that similar embodiments and features may arise or modifications and additions may be made without departing from the scope of these descriptions and the spirit of the appended claims.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter.

Example 1

Extraction of 42 g Peanut Husk Feedstock in a Batch Reactor

Examples 1-24 are directed to determining if various feedstock (peanut husks, wine pomace, apple peels, pinewood chips, soy hulls) can be used in making pulp for the paper industry, and whether the hydrothermal liquefaction process can be used to decrease or substitute the chemicals currently used in the pulp making process.

42.04 grams solid peanut husks (moisture content 16.15%) was combined with 428 mL 1% NaOH and added to a 500 mL Parr batch reactor (Model No. 4848). The reactor was preheated 21 minutes prior to the addition of the peanut husks and NaOH. The temperature and pressure were recorded at various timepoints, as set forth in Table 1, below.

The maximum temperature was 164° C., the maximum pressure was 84 psi, the pH was 7.5, and 1.68 mg/mL soluble sugars was recovered.

TABLE 1

Temperature and Pressure Measurements of Peanut Husk Feedstock

| Time (min.) | Temperature (° C.) | Pressure (psi) |
|---|---|---|
| 0 | 160 | 79 |
| 7 | 159 | 72 |
| 10 | 158 | 71 |
| 15 | 164 | 84 |
| 20 | 163 | 81 |

Example 2

Extraction of 23.74 g Peanut Husk Feedstock in a Batch Reactor 23.74 grams solid peanut husks (moisture content 16.15%) was combined with 465 mL 1% NaOH and added to the 500 mL batch reactor of Example 1. The reactor was preheated 29 minutes prior to the addition of the peanut husks and NaOH. The temperature and pressure were recorded at various timepoints, as set forth in Table 2, below.

The maximum temperature was 183° C., the maximum pressure was 171 psi, the pH was 8.25, and 0.62 mg/mL soluble sugars was recovered.

TABLE 2

Temperature and Pressure Measurements of Peanut Husks Feedstock

| Time (min.) | Temperature (° C.) | Pressure (psi) |
|---|---|---|
| 0 | 180 | 150 |
| 5 | 181 | 160 |
| 10 | 181 | 161 |
| 15 | 183 | 171 |
| 20 | 181 | 162 |

Example 3

Extraction of Chopped Peanut Husk Feedstock in a Batch Reactor, 20 Minute Preheating 30.58 grams chopped peanut husks (moisture content 16.15%) was combined with 474 mL 5% NaOH and added to the 500 mL batch reactor of Example 1. The reactor was preheated 20 minutes prior to the addition of the peanut husks and NaOH. The temperature and pressure were recorded at various timepoints, as set forth in Table 3, below.

The maximum temperature was 176° C., the maximum pressure was 1272 psi, the pH was 13.79, and 3.36 mg/mL soluble sugars was recovered.

TABLE 3

Temperature and Pressure Measurements of Chopped Peanut Husks Feedstock

| Time (min.) | Temperature (° C.) | Pressure (psi) |
|---|---|---|
| 0 | 174 | 965 |
| 5 | 173 | 721 |
| 10 | 176 | 1230 |
| 15 | 175 | 869 |
| 20 | 174 | 925 |

Example 4

Extraction of Chopped Peanut Husk Feedstock in a Batch Reactor, 36 Minute Preheating 30.98 grams chopped peanut husks (moisture content 16.15%) was combined with 475 mL 5% NaOH and added to the 500 mL batch reactor of Example 1. The reactor was preheated 36 minutes prior to the addition of the peanut husks and NaOH. The temperature and pressure were recorded at various timepoints, as set forth in Table 4, below.

The maximum temperature was 205° C., the maximum pressure was 1400 psi, the minimum pressure was 149 psi, the pH was 13.89, and 2.5 mg/mL soluble sugars was recovered.

TABLE 4

Temperature and Pressure Measurements of Chopped Peanut Husk Feedstock

| Time (min.) | Temperature (° C.) | Pressure (psi) |
|---|---|---|
| 0 | 191 | 825 |
| 5 | 200 | 720 |
| 10 | 192 | 154 |
| 15 | 189 | 149 |
| 20 | 198 | 184 |
| 25 | 198 | 173 |
| 30 | 195 | 170 |
| 35 | 202 | 277 |
| 40 | 201 | 222 |
| 45 | 200 | 195 |

Example 5

Extraction of 31.1 g Grape and 10 g Stem Feedstock in a Batch Reactor, 2.5% NaOH 31.10 grams grapes (moisture content 75.25%) and 10.01 grams grape stems (41.35% moisture content) were combined with 470 mL 2.5% NaOH and added to the 500 mL batch reactor of Example 1. The reactor was preheated 15 minutes prior to the addition of the grapes, stems, and NaOH. The temperature and pressure were recorded at various timepoints, as set forth in Table 5, below.

The maximum temperature was 132° C., the maximum pressure was 1500 psi, the pH was 13.63, and 1.67 mg/mL soluble sugars was recovered.

TABLE 5

Temperature and Pressure Measurements of Grape and Stem Feedstock

| Time (min.) | Temperature (° C.) | Pressure (psi) |
|---|---|---|
| 0 | 132 | 1300 |
| 5 | 132 | 920 |
| 10 | 129 | 500 |
| 15 | 128 | 630 |
| 20 | 130 | 760 |

Example 6

Extraction of 15.23 g Grape and 21.53 g Stem Feedstock in a Batch Reactor, 2.5% NaOH 15.23 grams grapes (moisture content 75.25%) and 21.53 grams grape stems (moisture content 41.35%) were combined with 460 mL 2.5% NaOH and added to the 500 mL batch reactor of Example 1. The reactor was preheated 15 minutes prior to the addition of the grapes, stems, and NaOH. The temperature and pressure were recorded at various timepoints, as set forth in Table 6, below.

The maximum temperature was 157° C., the maximum pressure was 1300 psi, the pH was 13.86, and 0.63 mg/mL soluble sugars was recovered.

TABLE 6

Temperature and Pressure Measurements of Grape and Stem Feedstock

| Time (min.) | Temperature (° C.) | Pressure (psi) |
|---|---|---|
| 0 | 155 | 1300 |
| 5 | 157 | 900 |
| 10 | 154 | 900 |

Example 7

Extraction of 13.82 g Grape and 21.75 g Stem Feedstock in a Batch Reactor, 1.5% NaOH 13.82 grams grapes (moisture content 75.25%) and 21.75 grams grape stems (moisture content 41.35%) were combined with 455 mL 1.5% NaOH and added to the 500 mL batch reactor of Example 1. The reactor was preheated 20 minutes prior to the addition of the grapes, stems, and NaOH. The temperature and pressure were recorded at various timepoints, as set forth in Table 7, below.

The maximum temperature was 174° C., the maximum pressure was 1240 psi, the pH was 13.35, and 2.12 mg/mL soluble sugars was recovered.

TABLE 7

Temperature and Pressure Measurements of Grape and Stem Feedstock

| Time (min.) | Temperature (° C.) | Pressure (psi) |
|---|---|---|
| 0 | 170 | 900 |
| 5 | 174 | 1200 |
| 10 | 171 | 1050 |
| 15 | 172 | 966 |
| 20 | 170 | 1020 |

Example 8

Extraction of Grape Stem Feedstock in a Batch Reactor 20.56 grams grape stems (moisture content 41.35%) was combined with 465 mL 2.5% NaOH and added to the 500 mL batch reactor of Example 1. The reactor was preheated 25 minutes prior to the addition of the stems and NaOH. The temperature and pressure were recorded at various timepoints, as set forth in Table 8, below.

The maximum temperature was 183° C., the maximum pressure was 840 psi, the pH was 13.69, and 2.22 mg/mL soluble sugars was recovered.

TABLE 8

Temperature and Pressure Measurements of Grape Stem Feedstock

| Time (min.) | Temperature (° C.) | Pressure (psi) |
|---|---|---|
| 0 | 178 | 300 |
| 5 | 180 | 316 |
| 10 | 180 | 430 |
| 15 | 183 | 800 |
| 20 | 179 | 310 |

Example 9

Extraction of Apple Peel Feedstock in a Batch Reactor, 1.5% NaOH 72.71 grams apple peel (moisture content 78.39%) was combined with 433 mL 1.5% NaOH and added to the 500 mL batch reactor of Example 1. The reactor was preheated 15 minutes prior to the addition of the apple peels and NaOH. The temperature and pressure were recorded at various timepoints, as set forth in Table 9, below.

The maximum temperature was 139° C., the maximum pressure was 1300 psi, the pH was 13.29, and 3.98 mg/mL soluble sugars was recovered.

TABLE 9

Temperature and Pressure Measurements of Apple Peel Feedstock

| Time (min.) | Temperature (° C.) | Pressure (psi) |
|---|---|---|
| 0 | 138 | 1000 |
| 3 | 139 | 1020 |

Example 10

Extraction of Apple Peel Feedstock in a Batch Reactor, 0.75% NaOH 78.77 grams apple peel (moisture content 78.39%) was combined with 425 mL 0.75% NaOH and added to the 500 mL batch reactor of Example 1. The reactor was preheated 15 minutes prior to the addition of the apple peels and NaOH. The temperature and pressure were recorded at various timepoints, as set forth in Table 10, below.

The maximum temperature was 136° C., the maximum pressure was 1600 psi, the pH was 10.85, and 4.91 mg/mL soluble sugars was recovered.

TABLE 10

Temperature and Pressure Measurements of Apple Peel Feedstock

| Time (min.) | Temperature (° C.) | Pressure (psi) |
|---|---|---|
| 0 | 136 | 1500 |
| 3 | 135 | 1100 |
| 5 | 135 | 1200 |

Example 11

Extraction of 74.73 g Apple Peel Feedstock in a Batch Reactor, 2.5% NaOH 74.73 grams apple peel (moisture content 78.39%) was combined with 420 mL 2.5% NaOH and added to the 500 mL batch reactor of Example 1. The reactor was preheated 15 minutes prior to the addition of the apple peels and NaOH. The temperature and pressure were recorded at various timepoints, as set forth in Table 11, below.

The maximum temperature was 170° C., the maximum pressure was 1500 psi, the pH was 13.40, and 1.85 mg/mL soluble sugars was recovered.

TABLE 11

Temperature and Pressure Measurements of Apple Peel Feedstock

| Time (min.) | Temperature (° C.) | Pressure (psi) |
|---|---|---|
| 0 | 165 | 500 |
| 5 | 167 | 1100 |
| 10 | 163 | 450 |
| 15 | 164 | 770 |
| 20 | 167 | 1266 |

Example 12

Extraction of 82 g Apple Peel Feedstock in a Batch Reactor, 2.5% NaOH 82.06 grams apple peel (moisture content 78.39%) was combined with 415 mL 2.5% NaOH and added to the 500 mL batch reactor of Example 1. The reactor was preheated 15 minutes prior to the addition of the apple peels and NaOH. The temperature and pressure were recorded at various timepoints, as set forth in Table 12, below.

The maximum temperature was 165° C., the maximum pressure was 1400 psi, the pH was 13.31, and 2.91 mg/mL soluble sugars was recovered.

TABLE 12

Temperature and Pressure Measurements of Apple Peel Feedstock

| Time (min.) | Temperature (° C.) | Pressure (psi) |
|---|---|---|
| 0 | 161 | 980 |
| 5 | 161 | 550 |
| 10 | 161 | 500 |
| 15 | 161 | 750 |

Example 13

Extraction of Pinewood Feedstock in a Batch Reactor, 1330 psi Maximum Pressure 12.57 grams pinewood solids (moisture content 12.43%) was combined with 490 mL 5.0% NaOH and added to the 500 mL batch reactor of Example 1. The reactor was preheated 14 minutes prior to the addition of the pinewood and NaOH. The temperature and pressure were recorded at various timepoints, as set forth in Table 13, below.

The maximum temperature was 141° C., the maximum pressure was 1330 psi, the pH was 13.57, and 0.65 mg/mL soluble sugars was recovered.

TABLE 13

Temperature and Pressure Measurements of Pinewood Feedstock

| Time (min.) | Temperature (° C.) | Pressure (psi) |
|---|---|---|
| 0 | 140 | 1200 |
| 5 | 140 | 966 |
| 10 | 139 | 800 |
| 15 | 141 | 1200 |
| 20 | 141 | 1330 |

Example 14

Extraction of Pinewood Feedstock in a Batch Reactor, 125 psi Maximum Pressure 16.01 grams pinewood solids (moisture content 12.43%) was combined with 455 mL 5.0% NaOH and added to the 500 mL batch reactor of Example 1. The reactor was preheated 20 minutes prior to the addition of the pinewood and NaOH. The temperature and pressure were recorded at various timepoints, as set forth in Table 14, below.

The maximum temperature was 179° C., the maximum pressure was 125 psi, the pH was 13.45, and 2.18 mg/mL soluble sugars was recovered.

TABLE 14

Temperature and Pressure Measurements of Pinewood Feedstock

| Time (min.) | Temperature (° C.) | Pressure (psi) |
|---|---|---|
| 0 | 176 | 122 |
| 5 | 175 | 112 |
| 10 | 174 | 114 |
| 15 | 177 | 122 |
| 20 | 179 | 125 |

Example 15

Extraction of Pinewood Feedstock in a Batch Reactor, 157 psi Maximum Pressure 17.25 grams solid pinewood (moisture content 12.43%) was combined with 460 mL 5% NaOH and added to the 500 mL batch reactor of Example 1. The reactor was preheated 20 minutes prior to the addition of the pinewood and NaOH. The temperature and pressure were recorded at various timepoints, as set forth in Table 15, below.

The maximum temperature was 187° C., the maximum pressure was 157 psi, the pH was 13.61, and 1.90 mg/mL soluble sugars was recovered.

TABLE 15

Temperature and Pressure Measurements of Pinewood Feedstock

| Time (min.) | Temperature (° C.) | Pressure (psi) |
|---|---|---|
| 0 | 186 | 157 |
| 5 | 183 | 138 |
| 10 | 186 | 144 |
| 15 | 187 | 150 |
| 20 | 186 | 144 |
| 25 | 187 | 150 |
| 30 | 187 | 146 |

Example 16

Extraction of Pinewood Feedstock in a Batch Reactor, 1500 psi Maximum Pressure 17.70 grams solid pinewood (moisture content 12.43%) was combined with 470 mL 5% NaOH and added to the 500 mL batch reactor of Example 1. The reactor was preheated 20 minutes prior to the addition of the pinewood and NaOH. The temperature and pressure were recorded at various timepoints, as set forth in Table 16, below.

The maximum temperature was 185° C., the maximum pressure was 1500 psi, the pH was 13.60, and 1.89 mg/mL soluble sugars was recovered.

TABLE 16

Temperature and Pressure Measurements of Pinewood Feedstock

| Time (min.) | Temperature (° C.) | Pressure (psi) |
|---|---|---|
| 0 | 180 | 1100 |
| 5 | 181 | 1300 |
| 10 | 185 | 1190 |
| 15 | 182 | 600 |
| 20 | 180 | 330 |
| 25 | 180 | 520 |
| 30 | 186 | 660 |
| 35 | 180 | 600 |
| 40 | 181 | 1200 |

Example 17

Extraction of Soy Hull Feedstock in a Batch Reactor, 162° C./1200 psi Maximum Temperature/Pressure 26.21 grams soy hull solids (moisture content 9.35%) was combined with 470 mL 2.5% NaOH and added to the 500 mL batch reactor of Example 1. The reactor was preheated 20 minutes prior to the addition of the soy hulls and NaOH. The temperature and pressure were recorded at various timepoints, as set forth in Table 17, below.

The maximum temperature was 162° C., the maximum pressure was 1200 psi, the pH was 13.13, and 3.94 mg/mL soluble sugars was recovered.

TABLE 17

Temperature and Pressure Measurements of Soy Hull Feedstock

| Time (min.) | Temperature (° C.) | Pressure (psi) |
|---|---|---|
| 0 | 158 | 1100 |
| 5 | 160 | 990 |
| 10 | 158 | 640 |

TABLE 17-continued

Temperature and Pressure Measurements of Soy Hull Feedstock

| Time (min.) | Temperature (° C.) | Pressure (psi) |
|---|---|---|
| 15 | 160 | 1021 |
| 20 | 160 | 770 |

Example 18

Extraction of Soy Hull Feedstock in a Batch Reactor, 145 psi Maximum Pressure 30.19 grams soy hull solids (moisture content 9.35%) was combined with 470 mL 2.5% NaOH and added to the 500 mL batch reactor of Example 1. The reactor was preheated 20 minutes prior to the addition of the soy hulls and NaOH. The temperature and pressure were recorded at various timepoints, as set forth in Table 18, below.

The maximum temperature was 170° C., the maximum pressure was 145 psi, the pH was 13.44, and 3.78 mg/mL soluble sugars was recovered.

TABLE 18

Temperature and Pressure Measurements of Soy Hull Feedstock

| Time (min.) | Temperature (° C.) | Pressure (psi) |
|---|---|---|
| 0 | 170 | 141 |
| 5 | 170 | 121 |
| 10 | 165 | 98 |
| 15 | 168 | 120 |
| 20 | 170 | 132 |

Example 19

Extraction of Soy Hull Feedstock in a Batch Reactor, 180° C./1200 psi Maximum Temperature/Pressure 30.45 grams soy hull solids (moisture content 9.35%) was combined with 465 mL 2.5% NaOH and added to the 500 mL batch reactor of Example 1. The reactor was preheated 20 minutes prior to the addition of the soy hulls and NaOH. The temperature and pressure were recorded at various timepoints, as set forth in Table 19, below.

The maximum temperature was 180° C., the maximum pressure was 1200 psi, the pH was 13.39, and 3.04 mg/mL soluble sugars was recovered.

TABLE 19

Temperature and Pressure Measurements of Soy Hull Feedstock

| Time (min.) | Temperature (° C.) | Pressure (psi) |
|---|---|---|
| 0 | 173 | 550 |
| 5 | 179 | 1180 |
| 10 | 175 | 570 |
| 15 | 172 | 242 |
| 20 | 177 | 800 |

Example 20

Extraction of Soy Hull Feedstock in a Batch Reactor, 1150 psi Maximum Pressure 30.40 grams soy hull solids (moisture content 9.35%) wase combined with 470 mL 2.5% NaOH and added to the 500 mL batch reactor of Example 1. The reactor was preheated 18 minutes prior to the addition of the soy hulls and NaOH. The temperature and pressure were recorded at various timepoints, as set forth in Table 20, below.

The maximum temperature was 170° C., the maximum pressure was 1150 psi, the pH was 13.45, and 3.65 mg/mL soluble sugars was recovered.

TABLE 20

Temperature and Pressure Measurements of Soy Hull Feedstock

| Time (min.) | Temperature (° C.) | Pressure (psi) |
|---|---|---|
| 0 | 165 | 538 |
| 5 | 170 | 920 |
| 10 | 167 | 405 |
| 15 | 166 | 580 |
| 20 | 169 | 810 |

Example 21

Extraction of Soy Hull Feedstock in a Batch Reactor, 1000 psi Maximum Pressure 30.39 grams soy hull solids (moisture content 9.35%) was combined with 460 mL 2.5% NaOH and added to the 500 mL batch reactor of Example 1. The reactor was preheated 18 minutes prior to the addition of the soy hulls and NaOH. The temperature and pressure were recorded at various timepoints, as set forth in Table 21, below.

The maximum temperature was 185° C., the maximum pressure was 1000 psi, the pH was 13.41, and 3.02 mg/mL soluble sugars was recovered.

TABLE 21

Temperature and Pressure Measurements of Soy Hull Feedstock

| Time (min.) | Temperature (° C.) | Pressure (psi) |
|---|---|---|
| 0 | 179 | 323 |
| 5 | 182 | 305 |
| 10 | 181 | 410 |
| 15 | 185 | 940 |
| 20 | 183 | 630 |

Example 22

Extraction of Soy Hull Feedstock in a Batch Reactor, 1300 psi Maximum Pressure 30.74 grams soy hull solids (moisture content 9.35%) was combined with 460 mL 2.5% NaOH and added to the 500 mL batch reactor of Example 1. The reactor was preheated 20 minutes prior to the addition of the soy hulls and NaOH. The temperature and pressure were recorded at various timepoints, as set forth in Table 22, below.

The maximum temperature was 178° C., the maximum pressure was 1300 psi, the pH was 13.40, and 2.67 mg/mL soluble sugars was recovered.

TABLE 22

Temperature and Pressure Measurements of Soy Hull Feedstock

| Time (min.) | Temperature (° C.) | Pressure (psi) |
|---|---|---|
| 0 | 178 | 1300 |
| 5 | 174 | 1100 |
| 10 | 175 | 800 |
| 15 | 177 | 1050 |
| 20 | 176 | 1040 |
| 25 | 178 | 1050 |
| 30 | 177 | 810 |

Example 23

Extraction of Soy Hull Feedstock in a Batch Reactor, 1250 psi Maximum Pressure

31.45 grams soy hull solids (moisture content 9.35%) was combined with 455 mL 2.5% NaOH and added to the 500 mL batch reactor of Example 1. The reactor was preheated 20 minutes prior to the addition of the soy hulls and NaOH. The temperature and pressure were recorded at various timepoints, as set forth in Table 23, below.

The maximum temperature was 193° C., the maximum pressure was 1250 psi, the pH was 13.36, and 2.79 mg/mL soluble sugars was recovered.

TABLE 23

Temperature and Pressure Measurements of Soy Hull Feedstock

| Time (min.) | Temperature (° C.) | Pressure (psi) |
|---|---|---|
| 0 | 188 | 900 |
| 5 | 193 | 1030 |
| 10 | 188 | 450 |
| 15 | 189 | 990 |
| 20 | 191 | 1160 |

Example 24

Extraction of Soy Hull Feedstock in a Batch Reactor, 470 psi Maximum Pressure

31.57 grams soy hull solids (moisture content 9.35%) was combined with 450 mL 2.5% NaOH and added to the 500 mL batch reactor of Example 1. The reactor was preheated 20 minutes prior to the addition of the soy hulls and NaOH. The temperature and pressure were recorded at various timepoints, as set forth in Table 24, below.

The maximum temperature was 199° C., the maximum pressure was 470 psi, the pH was 13.31, and 2.58 mg/mL soluble sugars was recovered.

TABLE 24

Temperature and Pressure Measurements of Soy Hull Feedstock

| Time (min.) | Temperature (° C.) | Pressure (psi) |
|---|---|---|
| 0 | 194 | 205 |
| 5 | 193 | 196 |
| 10 | 194 | 205 |
| 15 | 196 | 250 |
| 20 | 197 | 240 |
| 25 | 199 | 470 |

Conclusions from Examples 1-24

Four samples—Example 12 (apple peel), Examples 15 and 16 (pine wood), and Example 20 (soy hulls)—were found to perform the best for making pulp for the paper industry. This determination was based on the physical examination of the samples. It was concluded that the most appropriate conditions to make pulp from pinewood were about 182° C., about 800 psi, and a residence time of 30-40 minutes. By increasing the NaOH concentration from 5% to 7% or 10%, the residence time can be shortened. For apple peel, the most appropriate conditions were about 161° C., about 800 psi, about 2.5% NaOH, and about a 15-minute residence time. Although the conditions varied greatly in the soy hull examples, the results suggest that NaOH concentration may play a crucial role, and concentrations of NaOH below 2.5% are too low.

The data set forth herein illustrates that good quality pulp was generated using far less quantities of NaOH compared to traditional methods of making pulp for the paper industry.

Examples 25-34

Examples 25-34 are directed to methods and processes for producing paper products from biomass (i.e., tobacco biomass) using subcritical water technology (or "hydrothermal liquefaction") to decrease or substitute the chemicals that are currently used in the pulp making process. In addition, Examples 25-34 are directed to determining whether a hydrothermal liquefaction process (subcritical water) can be used to decrease or substitute the chemicals currently used in the pulp making process.

Five sample sets of pulp were produced, as set forth in Table 25 below.

TABLE 25

Pulp Sample Sets Used in Examples 25-34

| Sample # | Pressure (psi) | Time (min) | Temp (° C.) | Soda (%) | Sample A | Sample B | Sample C |
|---|---|---|---|---|---|---|---|
| Control | 1000 | 10 | 165 C. | 25 | 5 kg pulp | 5 gal liquor (diluted) | 5 L liquor (concentrated) |
| Set 1 | 1000 | 5 | 165 | 0 | 5 kg pulp | 5 gal liquor (diluted) | 5 L liquor (concentrated) |
| Set 2 | 1000 | 10 | 165 | 0 | 5 kg pulp | 5 gal liquor (diluted) | 5 L liquor (concentrated) |
| Set 3 | 1000 | 5 | 225 | 0 | 5 kg pulp | 5 gal liquor (diluted) | 5 L liquor (concentrated) |

TABLE 25-continued

Pulp Sample Sets Used in Examples 25-34

| Sample # | Pressure (psi) | Time (min) | Temp (° C.) | Soda (%) | Sample A | Sample B | Sample C |
|---|---|---|---|---|---|---|---|
| Set 4 | 1000 | 10 | 225 | 0 | 5 kg pulp | 5 gal liquor (diluted) | 5 L liquor (concentrated) |

In these experiments, a bench-level reactor (Parr) was used with 500 mL of volume. The dried tobacco stalks were hammer milled, with a desired particle size of 4.5 mm. The tobacco material was treated under various conditions (temperature; pressure; with & without NaOH; residence time; with & without pretreatment) as set forth in Examples 25-34 below.

Example 25

Extraction of Tobacco Feedstock in Batch Reactor Using Water, Max Pressure 300 psi 41.69 grams of the milled tobacco stalks (moisture content 10.46%) was combined with 410 mL deionized water and added to the 500 mL batch reactor of Example 1. The reactor was preheated 25 minutes prior to the addition of the tobacco and water. The temperature and pressure were recorded at various timepoints, as set forth in Table 26, below.

The maximum temperature was 201° C., the maximum pressure was 300 psi, the pH was 4.65, and 0.39 mg/mL soluble sugars was recovered.

TABLE 26

Temperature and Pressure Measurements of Tobacco Feedstock

| Time (min.) | Temperature (° C.) | Pressure (psi) |
|---|---|---|
| 0 | 200 | 238 |
| 10 | 197 | 261 |
| 20 | 201 | 288 |
| 30 | 198 | 300 |

Example 26

Extraction of Tobacco Feedstock in Batch Reactor Using Water, Max Pressure 930 psi 40.84 grams of the milled tobacco stalks (moisture content 10.46%) was combined with 453 mL deionized water and added to the 500 mL batch reactor of Example 1. The reactor was preheated 20 minutes prior to the addition of the tobacco and water. The temperature and pressure were recorded at various timepoints, as set forth in Table 27, below.

The maximum temperature was 180° C., the maximum pressure was 930 psi, the pH was 5.19, and 0.46 mg/mL soluble sugars was recovered.

TABLE 27

Temperature and Pressure Measurements of Tobacco Feedstock

| Time (min.) | Temperature (° C.) | Pressure (psi) |
|---|---|---|
| 0 | 180 | 541 |
| 10 | 180 | 354 |
| 20 | 180 | 683 |
| 30 | 180 | 904 |

Example 27

Extraction of Tobacco Feedstock in Batch Reactor Using Water, Max Pressure 1500 psi 41.70 grams of the milled tobacco stalks (moisture content 10.46%) was combined with 460 mL deionized water and added to the 500 mL batch reactor of Example 1. The reactor was preheated 20 minutes prior to the addition of the tobacco and water. The temperature and pressure were recorded at various timepoints, as set forth in Table 28, below.

The maximum temperature was 167° C., the maximum pressure was 1500 psi, the pH was 5.37, and 0.40 mg/mL soluble sugars was recovered.

TABLE 28

Temperature and Pressure Measurements of Tobacco Feedstock

| Time (min.) | Temperature (° C.) | Pressure (psi) |
|---|---|---|
| 0 | 160 | 1180 |
| 10 | 160 | 1060 |
| 20 | 167 | 514 |
| 30 | 161 | 145 |

Example 28

Extraction of Tobacco Feedstock in Batch Reactor Using NaOH, Max Pressure 1383 psi 41.32 grams of the milled tobacco stalks (moisture content 10.46%) was combined with 455 mL 5% NaOH and added to the 500 mL batch reactor of Example 1. The reactor was preheated 30 minutes prior to the addition of the tobacco and NaOH. The temperature and pressure were recorded at various timepoints, as set forth in Table 29, below.

The maximum temperature was 166° C., the maximum pressure was 1383 psi, the pH was 13.49, and 0.66 mg/mL soluble sugars was recovered.

TABLE 29

Temperature and Pressure Measurements of Tobacco Feedstock

| Time (min.) | Temperature (° C.) | Pressure (psi) |
|---|---|---|
| 0 | 166 | 623 |
| 10 | 166 | 715 |
| 20 | 158 | 324 |
| 30 | 166 | 800 |

Example 29

Extraction of Tobacco Feedstock in Batch Reactor Using NaOH, 23 min. Preheating 41.42 grams of the milled tobacco stalks (moisture content 10.46%) was combined with 455 mL 2.5% NaOH and added to the 500 mL batch reactor of Example 1. The reactor was preheated 23 minutes prior to the addition of the tobacco and NaOH. The temperature and pressure were recorded at various timepoints, as set forth in Table 30, below.

The maximum temperature was 170° C., the maximum pressure was 1500 psi, the pH was 13.29, and 0.48 mg/mL soluble sugars was recovered.

TABLE 30

Temperature and Pressure Measurements of Tobacco Feedstock in Reactor

| Time (min.) | Temperature (° C.) | Pressure (psi) |
|---|---|---|
| 0 | 165 | 700 |
| 10 | 164 | 346 |
| 20 | 170 | 1356 |

Example 30

Extraction of Pretreated Tobacco Feedstock in Batch Reactor Using NaOH

Tobacco stalks were boiled for about one hour and soaked in water overnight as a pretreatment step. 245 grams of pretreated tobacco stalks (moisture content 80.27%) was combined with 265 mL 2.5% NaOH and added to the 500 mL batch reactor of Example 1. The reactor was preheated 18 minutes prior to the addition of the tobacco and NaOH. The temperature and pressure were recorded at various timepoints, as set forth in Table 31, below.

The maximum temperature was 146° C., the maximum pressure was 1880 psi, the pH was 11.16, and 0.37 mg/mL soluble sugars was recovered.

TABLE 31

Temperature and Pressure Measurements of Tobacco Feedstock

| Time (min.) | Temperature (° C.) | Pressure (psi) |
|---|---|---|
| 0 | 146 | 1880 |
| 10 | 130 | 1190 |
| 20 | 143 | 695 |
| 30 | 142 | 425 |

Example 31

Extraction of Pretreated Tobacco Feedstock in Batch Reactor Using Water

Tobacco stalks were boiled for about one hour and soaked in water overnight as a pretreatment step. 269.04 grams pretreated tobacco stalks (moisture content 80.27%) was combined with 240 mL deionized water and added to the 500 mL batch reactor of Example 1. The reactor was preheated 20 minutes prior to the addition of the tobacco and water. The temperature and pressure were recorded at various timepoints, as set forth in Table 32, below.

The maximum temperature was 130° C., the maximum pressure was 1750 psi, the pH was 5.44, and 0.44 mg/mL soluble sugars was recovered.

TABLE 32

Temperature and Pressure Measurements of Tobacco Feedstock

| Time (min.) | Temperature (° C.) | Pressure (psi) |
|---|---|---|
| 0 | 124 | 1600 |
| 10 | 126 | 839 |
| 20 | 124 | 1100 |
| 30 | 130 | 1750 |

Example 32

Extraction of Tobacco Feedstock in Batch Reactor Using Water, Max Pressure 260 psi 63.24 grams of the milled tobacco stalks (moisture content 10.46%) was combined with 400 mL deionized water and added to the 500 mL batch reactor of Example 1. The reactor was preheated 25 minutes prior to the addition of the tobacco and water. The temperature and pressure were recorded at various timepoints, as set forth in Table 33, below.

The maximum temperature was 187° C., the maximum pressure was 260 psi, the pH was 4.82, and 0.83 mg/mL soluble sugars was recovered.

TABLE 33

Temperature and Pressure Measurements of Tobacco Feedstock

| Time (min.) | Temperature (° C.) | Pressure (psi) |
|---|---|---|
| 0 | 180 | 169 |
| 10 | 173 | 206 |
| 20 | 187 | 260 |
| 30 | 183 | 246 |

Example 33

Extraction of Tobacco Feedstock in Batch Reactor Using NaOH, Max Pressure 1550 psi 50.13 grams of the milled tobacco stalks (moisture content 10.46%) was combined with 445 mL 2.5% NaOH and added to the 500 mL batch reactor of Example 1. The reactor was preheated 30 minutes prior to the addition of the tobacco and NaOH. The temperature and pressure were recorded at various timepoints, as set forth in Table 34, below.

The maximum temperature was 174° C., the maximum pressure was 1550 psi, the pH was 13.29, and 0.56 mg/mL soluble sugars was recovered.

TABLE 34

Temperature and Pressure Measurements of Tobacco Feedstock

| Time (min.) | Temperature (° C.) | Pressure (psi) |
|---|---|---|
| 0 | 173 | 1100 |
| 10 | 170 | 580 |
| 20 | 171 | 1100 |
| 30 | 170 | 990 |

Example 34

Extraction of Tobacco Feedstock in Batch Reactor Using Water, Max Pressure 1140 psi 51 grams of the milled tobacco stalks (moisture content 10.46%) was combined with 450 mL deionized water and added to the 500 mL batch reactor of Example 1. The reactor was preheated 20 minutes prior to the addition of the tobacco and water. The temperature and pressure were recorded at various timepoints, as set forth in Table 35, below.

The maximum temperature was 170° C., the maximum pressure was 1140 psi, the pH was 4.92, and 0.61 mg/mL soluble sugars was recovered.

TABLE 35

Temperature and Pressure Measurements of Tobacco Feedstock

| Time (min.) | Temperature (° C.) | Pressure (psi) |
|---|---|---|
| 0 | 165 | 1120 |
| 10 | 170 | 1140 |
| 20 | 166 | 332 |
| 30 | 162 | 148 |

Conclusions from Examples 25-34

It was observed that when temperatures over 180° C. were used, the final content in solids was very low. The same results were obtained when concentrations over 5% NaOH were used (the solids were liquefied during the reaction). More favorable results were obtained when only water or 2.5% NaOH was used as the reaction media. The data indicates that the most favorable conditions for making good quality pulp are about 170° C., about 1000 psi, and a residence time of about 20-30 minutes.

Figure 5:
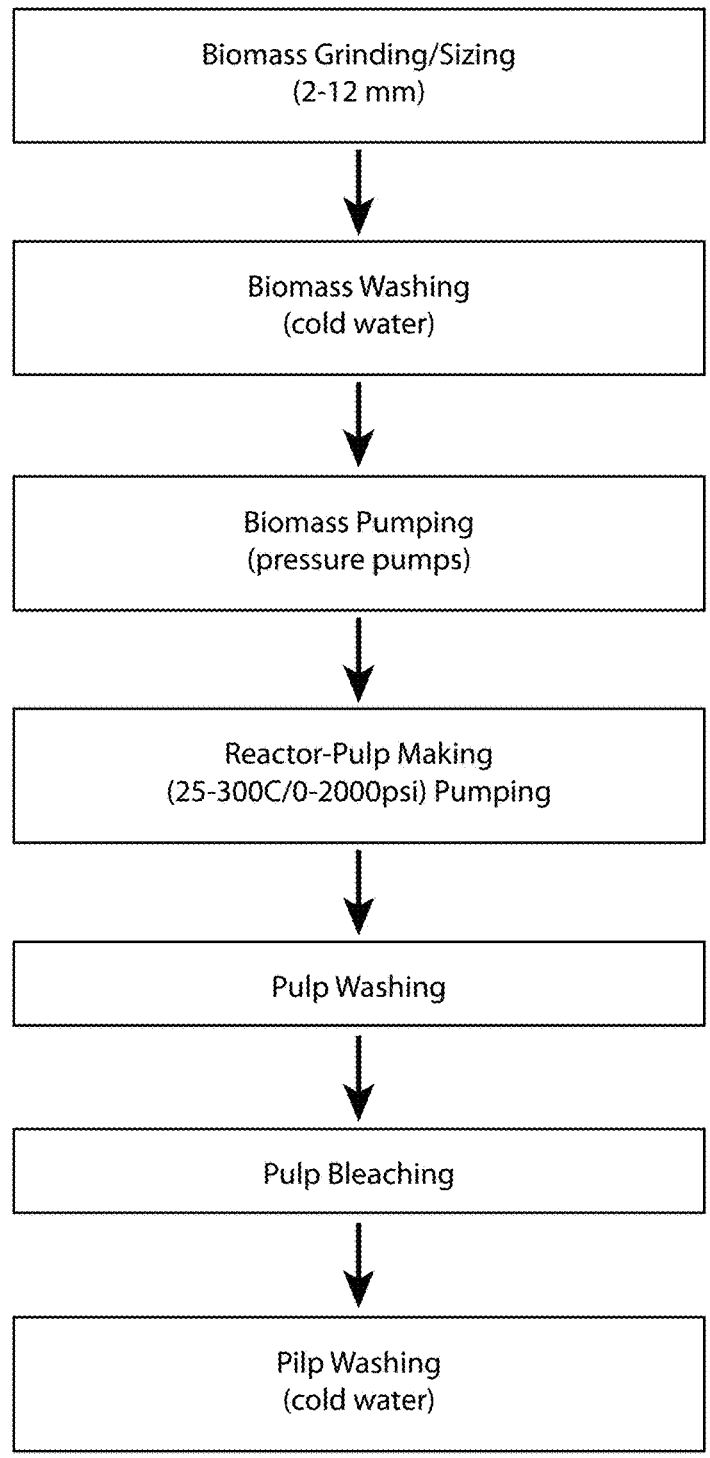
FIG. 5 is a flow chart of a process used to make pulp from biomass in accordance with some embodiments of the presently disclosed subject matter.
Figure 6A:
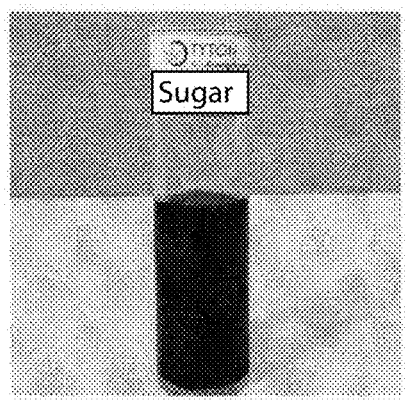
FIG. 6a is a photograph of fermentable carbohydrates (sugar) manufactured in accordance with some embodiments of the presently disclosed subject matter.
Figure 6B:
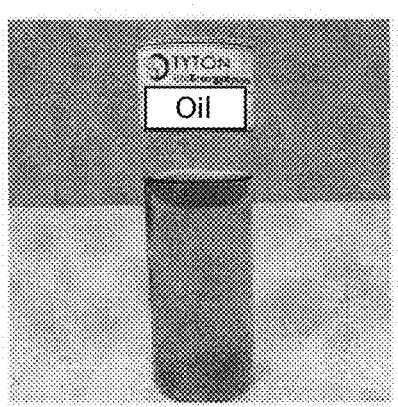
FIG. 6b is a photograph of oil manufactured in accordance with some embodiments of the presently disclosed subject matter.
Figure 6C:
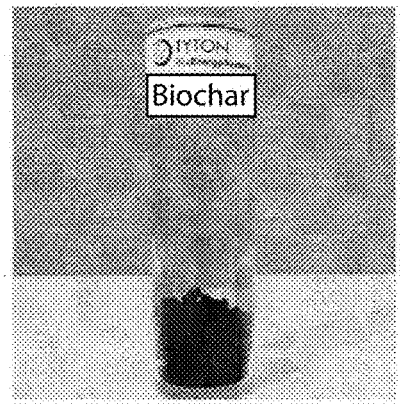
FIG. 6c is a photograph of biochar manufactured in accordance with some embodiments of the presently disclosed subject matter.
Figure 6D:
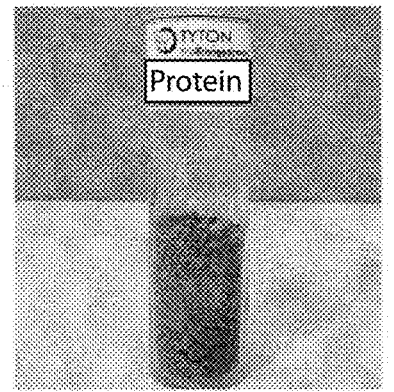
FIG. 6d is a photograph of bio-derivatives (protein) manufactured in accordance with some embodiments of the presently disclosed subject matter.
Figure 6E:
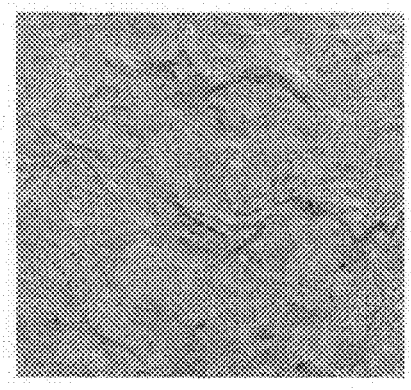
FIG. 6e is a photograph of paper manufactured in accordance with some embodiments of the presently disclosed subject matter.
Figure 6F:
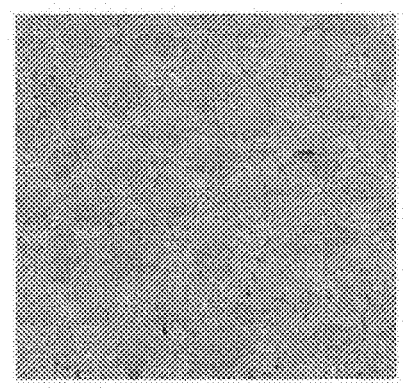
FIG. 6f is a photograph of cardboard manufactured in accordance with some embodiments of the presently disclosed subject matter.

Similar results were obtained with a pilot scale extractor similar to the one shown in FIG. 1. The results produced the first piece of paper out of tobacco waste by using hydrothermal treatment and decreasing significantly the amount of NaOH used in pulp making process from 27% (standard in the industry) to 2.5%. FIGS. 5a and 5b illustrate photographs of paper (5a) and cardboard (5b) constructed from tobacco lignocellulosic material waste. Tables 36-38 below summarize the results of Examples 25-32 with the pilot scale reactor. Table 39 is provided for reference.

TABLE 36

Pilot Scale Reactor Testing of Examples 25-32

| Sample No. | Dry solids:solvent | Solvent NaOH (%) | Pressure (psi) | Temp. (° C.) | Residence (min) | pH | Total sugar (mg/mL) |
|---|---|---|---|---|---|---|---|
| Control | 1:15 | | | | | | |
| 1 | 1:15 | 2.5 | 1000 | 170 | 20 | 12 | 0.67 |
| 2 | 1:15 | 2.5 | 700 | 165 | 20 | 12 | 2.88 |
| 3 | 1:15 | 2.5 | 700 | 150 | 20 | 11.5 | 2.42 |
| 4 | 1:15 | 2 | 800 | 110 | 20 | 11 | 1.49 |
| 5 | 1:15 | 2 | 900 | 200 | 10 | 11 | 1.50 |
| 6 | 1:15 | 2 | 900 | 200 | 20 | 11 | 2.71 |
| 7 | 1:15 | 2 | 800 | 210 | 20 | 10.5 | 1.11 |
| 8 | 1:15 | 2 | 850 | 220 | 20 | 10 | 1.28 |

Table 37 illustrates properties of unrefined pulps versus pulp produced from tobacco examples (dried tobacco biomass). Process conditions for Sample 1 (S1): 185° C., 2.5% NaOH, 900 psi; Sample 2 (S2): 180° C., 2.5% NaOH, 900 psi; Sample 3 (S3): 175° C., 2.5% NaOH, 900 psi; Sample 4 (S4): 170° C., 2.5% NaOH, 900 psi.

TABLE 37

Properties of Unrefined Pulps Versus Pulp Produced from Examples

| Process | Alkaline sulfate | Soda | Soda | Soda | Control | S1 | S2 | S3 | S4 |
|---|---|---|---|---|---|---|---|---|---|
| PFI, TAPPI (revs) | 0 | 0 | 0 | 0 | N/A | 0 | 0 | 0 | 0 |
| C.S. Freeness (mL) | 41.3 | 638 | 562 | 671 | N/A | 394 | 184 | 148 | 165 |
| Basis weight, conditioned (g/m³) | 63.07 | 67.49 | 66.81 | 68.43 | N/A | 63.61 | 63.68 | 66.56 | 65.24 |

TABLE 37-continued

Properties of Unrefined Pulps Versus Pulp Produced from Examples

| Process | Alkaline sulfate | Soda | Soda | Soda | Control | S1 | S2 | S3 | S4 |
|---|---|---|---|---|---|---|---|---|---|
| Bulk (cc/g) | 1.48 | 1.88 | 1.75 | 1.90 | N/A | 1.79 | 1.36 | 1.33 | 1.41 |
| Burst index (kPa-m$^2$/g) | 1.37 | 0.58 | 0.54 | 0.37 | N/A | 0.38 | 1.22 | 1.42 | 1.48 |
| Tear index (mN-m$^2$/g) | 4.71 | 2.56 | 4.06 | 3.09 | N/A | 1.70 | 1.88 | 2.17 | 2.59 |
| Tensile index (N-m/g) | 37.3 | 16.6 | 15.2 | 12.6 | N/A | 13.0 | 38.7 | 44.6 | 44.4 |
| Tensile (km) | 3.81 | 1.69 | 1.55 | 1.29 | N/A | 1.33 | 3.94 | 4.55 | 4.53 |
| Stretch (%) | 1.15 | 0.56 | 0.34 | 0.27 | N/A | 0.22 | 0.84 | 0.99 | 1.12 |
| Tensile Energy Abs (J/m$^3$) | 18.6 | 5.41 | 3.00 | 2.12 | N/A | 1.70 | 12.7 | 18.7 | 21.1 |
| Internal Bond (0.001 ft-lb/in$^2$) | 173 | 44.9 | 44.4 | 47.2 | N/A | 100 | 233 | 207 | 177 |
| Brightness ISO handsheet (%) | 27.4 | 36.7 | 28.9 | 22.2 | N/A | 26.8 | 28.6 | 29.6 | 27.5 |
| Viscosity 0.5% CED (cPs) | 22.5 | 6.74 | 12.8 | 14.1 | 2.44 | 20.4 | 4.42 | 3.66 | 5.21 |
| Kappa Number | 35.8 | 12.2 | 25.5 | 30.1 | 51.4 | 35.8 | 14.6 | 14.2 | 16.1 |
| LWAFL (mm) | 0.75 | 0.70 | 0.77 | 0.77 | 0.53 | 0.45 | 0.44 | 0.46 | 0.48 |
| % fines, length weighted <0.2 mm (%) | 13.21 | 6.62 | 7.69 | 7.67 | 28.27 | 26.85 | 24.13 | 23.51 | 21.19 |

Table 38 illustrates properties of unrefined pulps versus pulp produced from tobacco examples (dried tobacco biomass). Process conditions for Sample 1 (S1): 185° C., 2.5% NaOH, 900 psi; Sample 2 (S2): 180° C., 2.5% NaOH, 900 psi; Sample 3 (S3): 175° C., 2.5% NaOH, 900 psi; Sample 4 (S4): 170° C., 2.5% NaOH, 900 psi.

TABLE 38

Properties of Unrefined Pulps Versus Pulp Produced from Examples

| Process | Alkaline sulfate | Soda | Soda | Soda | Control | S1 | S2 | S3 | S4 |
|---|---|---|---|---|---|---|---|---|---|
| PFI, TAPPI (revs) | 200 | 3200 | 2000 | 3400 | N/A | 100 | 0 | 0 | 0 |
| C.S. Freeness (mL) | 285 | 3.19 | 320 | 307 | N/A | 294 | 184 | 148 | 165 |
| Basis weight, conditioned (g/m$^3$) | 66.06 | 67.01 | 66.78 | 67.57 | N/A | 63.84 | 63.68 | 66.56 | 65.24 |
| Bulk (cc/g) | 1.41 | 1.45 | 1.49 | 1.49 | N/A | 1.78 | 1.36 | 1.33 | 1.41 |
| Burst index (kPa-m$^2$/g) | 1.99 | 2.32 | 1.69 | 1.87 | N/A | 0.45 | 1.22 | 1.42 | 1.48 |
| Tear index (mN-m$^2$/g) | 4.93 | 3.96 | 5.35 | 4.84 | N/A | 1.95 | 1.88 | 2.17 | 2.59 |
| Tensile index (N-m/g) | 47.2 | 41.2 | 37.8 | 40.9 | N/A | 14.8 | 38.7 | 44.6 | 44.4 |
| Tensile (km) | 4.81 | 4.25 | 3.86 | 4.17 | N/A | 1.51 | 3.94 | 4.55 | 4.53 |
| Stretch (%) | 1.34 | 1.96 | 1.47 | 1.71 | N/A | 0.29 | 0.84 | 0.99 | 1.12 |
| Tensile Energy Abs (J/m$^3$) | 27.9 | 37.1 | 25.6 | 33.1 | N/A | 2.45 | 12.7 | 18.7 | 21.1 |
| Internal Bond (0.001 ft-lb/in$^2$) | 204 | 100 | 111 | 124 | N/A | 115 | 233 | 207 | 177 |

TABLE 38-continued

Properties of Unrefined Pulps Versus Pulp Produced from Examples

| Process | Alkaline sulfate | Soda | Soda | Soda | Control | S1 | S2 | S3 | S4 |
|---|---|---|---|---|---|---|---|---|---|
| Brightness ISO handsheet (%) | 25.2 | 32.9 | 26.2 | 19.4 | N/A | 27.1 | 28.6 | 29.6 | 27.5 |

TABLE 39

Feedstock Chemical Composition (% Dry Material)

| Feedstocks | Lignin (%) | Cellulose (%) | Hemi-cellulose (%) | Note |
|---|---|---|---|---|
| Soybean Hulls | 2.0 | 46.0 | 18.0 | n/a |
| Peanut Hulls | 35.2 | 22.1 | 12.1 | n/a |
| Pine Wood (1) | 39.0 | 31.1 | 60.0 | Age 1-3 years |
| Pine Wood (2) | 30.4 | 42.5 | 22.9 | Age 21-25 years |
| Pine Wood (3) | 34.9 | 36.4 | 23.5 | Age >30 years |
| Wine Pomace (1) | 17.2 | 14.5 | 10.3 | Red grape |
| Wine Pomace (2) | 11.6 | 9.2 | 4.0 | White grape |
| Orange Peel (1) | 2.2 | 11.9 | 14.5 | n/a |
| Orange Peel (2) | 5.0 | 16.4 | 6.7 | n/a |
| Apple Peel | 15.3 | 39. | 19.2 | n/a |
| Wheat Straw | 14.1 | 38.6 | 32.6 | n/a |
| Corn Stover | 15.0 | 38.5 | 28.0 | n/a |
| Corn Cob | 14.6 | 43.2 | 31.8 | n/a |
| Tobacco Leaf | 4.0-5.0 | 17.0-20.0 | 15.0-19.0 | n/a |
| Tobacco Stalk | 17.0-21.0 | 30.0-34.0 | 18.0-26.0 | n/a |
| Sugarcane bagasse | 22.0 | 35.0 | 25.0 | n/a |
| Hemp | 12 | 58 | 16 | n/a |
| Rice Straw | 10 | 39 | 26 | n/a |

What is claimed is:

1. A system comprising:
a pre-processing portion having a mechanical processor/material handler for extraction of water soluble fermentable carbohydrates and preparation of material for further extraction;
an extractor portion comprising a reactor or a reactor assembly to which biomass and subcritical water is supplied, the reactor or reactor assembly having:
a first operating condition at a first pressure and a first temperature at a constant level that is held for a first defined period of time to break down carbohydrates of a first chain strength; and
a second operating condition at a second pressure and a second temperature at a constant level that is held for a defined second period of time to break down lignin and the remaining oligo-carbohydrates of a second chain strength and fatty acids, or
both the first operating condition and the second operating condition;
wherein the system is repeatable until the recovery rate of the fermentable carbohydrates, fatty acid, or both reaches a desired yield; and
wherein the reactor assembly comprises an assembly of one or more reactors followed by one or more pressure control valves, heat exchangers for cooling down the outputs from the reactor, and separators to collect valuable materials from the water phase and consequently recycle the water.

2. The system according to claim 1, wherein the mechanical processor/material handler of the pre-processing portion includes a mechanical press for primary extraction of soluble carbohydrates, a wet or dry mill operably coupled to a material feeding mechanism, or both, and a storage tank for mixing with water or other liquid.

3. The system of claim 2, wherein the reactor assembly comprises continuous-type reactors or batch-type reactors.

4. The system according to claim 1, further comprising a variable speed and flow rate pump that pumps the fermentable carbohydrates, fatty acid, or both downstream.

5. The system according to claim 1, further including:
a high pressure pump for increasing a pressure in the system, wherein a variable speed and flow rate are provided;
a pressure control valve for maintaining pressure in the first operating condition;
a pump for increasing the pressure of biomass in the flow channel to a second temperature and a second pressure; and
a pressure control valve for maintaining pressure in the second pressure and second temperature section.

6. The system according to claim 1, wherein first operating condition comprises a pressure of about 0-300 psi and temperature of up to about 180° C. and the second operating condition comprises a pressure of about 301-3000 psi and a temperature of about 180° C. to 350° C.

7. The system of claim 1, wherein the pre-processing and first and second operating conditions are controlled and monitored by a centralized computer software able to maintain constant a desired pressure, temperature, and flow rate for a desired period of time;
wherein the system comprises multiple sensors that are installed and connected to centralized computer managing software comprising a network in which technical information about major parameters such as pressure, temperature, flow, content level, is collected in real time, relayed to a managing system, and analyzed;
wherein the above parameters are controlled and modified in real time.

8. The system of claim 1, wherein the system is configured to produce as its final product feedstock constituents such as fermentable carbohydrates, fatty acids, and other compounds for biofuel production, biochar, pulp, cellulose, or raw materials for various industries, or combinations thereof from plant based materials, cotton linters, or putrescible waste.

9. The system of claim 1, wherein the system is modular and scalable, stationary or mobile;
wherein when in mobile form, the system can be mounted on one or more truck trailers, rail cars, shipping containers, other platforms used to transport from one site to another, or combinations thereof.

10. A method of producing biochar from plant based or putrescible materials with increased properties, said method comprising:
introducing biomass into the system of claim 1;
adding oil to the system during the production of biochar;
wherein the produced biochar exhibits increased thermal value compared to biochar produced without the additional of oil to the system during production.

11. The method of claim 10, wherein the biochar exhibits a thermal value in the range of about 20,000 to 30,000 BTU/pound, wherein about 14,000-16,700 BTU/pound is attributable to the added oil.

12. The method of claim 10, wherein the method is modular and scalable, stationary or mobile; and
wherein when in mobile form, the system can be mounted on one or more truck trailers, rail cars, shipping containers, other platforms used to transport from one site to another, or combinations thereof.

13. A method of producing pulp comprising:
processing a biomass into a processing size; and
using a subcritical water treatment process, treating the biomass with a catalyst that comprises an alkaline catalyst at a concentration of about 1.5 to 10 weight percent or less in a reactor assembly having:
a first operating condition at a first pressure and a first temperature at a constant level that is held for a first defined period of time to break down carbohydrates of a first chain strength; and
a second operating condition at a second pressure and a second temperature at a constant level that is held for a defined second period of time to break down lignin and the remaining oligo-carbohydrates of a second chain strength and fatty acids;
to produce a pulp product.

14. The method of claim 13, wherein the pulp product has fiber length of about 0.000001-12 mm.

15. The method of claim 13, wherein the method provides for continuous flow of material through the reactor such that the process provides for continuous manufacture of paper pulp product, cellulose, or combinations thereof.

16. The method of claim 13, wherein the method is modular and scalable, stationary or mobile; and
wherein when in mobile form, the system can be mounted on one or more truck trailers, rail cars, shipping containers, other platforms used to transport from one site to another, or combinations thereof.

17. Pulp, powdered cellulose, nano-cellulose, and dissolving cellulose produced from the method of claim 13, with fiber size of 0.000001-12 mm;
wherein soluble carbohydrates and other soluble materials in water are produced as co-products.

* * * * *